US007067487B2

(12) United States Patent
Langedijk

(10) Patent No.: US 7,067,487 B2
(45) Date of Patent: Jun. 27, 2006

(54) TRANSPORT PEPTIDES SUCH AS C-TERMINAL E$^{RNS}$ PEPTIDE AND ANALOGUES THEREOF

(75) Inventor: Johannes Petrus M. Langedijk, Amsterdam (NL)

(73) Assignee: Pepscan Systems B.V., Lelystad (NL)

( * ) Notice: Subject to any disclaimer, the term of this patent is extended or adjusted under 35 U.S.C. 154(b) by 91 days.

(21) Appl. No.: 10/335,057

(22) Filed: Dec. 30, 2002

(65) Prior Publication Data
US 2003/0224016 A1 Dec. 4, 2003

Related U.S. Application Data

(63) Continuation of application No. PCT/NL01/00484, filed on Jun. 28, 2001.

(30) Foreign Application Priority Data
Jun. 28, 2000 (EP) .................... 00202255

(51) Int. Cl.
*A61K 39/12* (2006.01)
*C07K 14/18* (2006.01)
*C07K 16/10* (2006.01)
*G01N 33/569* (2006.01)

(52) U.S. Cl. .................. 514/12; 424/186.1; 424/211.1; 530/324

(58) Field of Classification Search ................ 530/300, 530/322, 324, 350, 395; 514/8, 12; 435/200; 424/186.1, 211.1, 94.61
See application file for complete search history.

(56) References Cited

U.S. PATENT DOCUMENTS

| 5,877,153 | A | | 3/1999 | Harris et al. .................. 514/13 |
| 6,149,911 | A | * | 11/2000 | Binz et al. ................ 424/192.1 |
| 6,200,955 | B1 | | 3/2001 | Harris et al. .................. 514/13 |
| 6,261,569 | B1 | * | 7/2001 | Comis et al. ............. 424/204.1 |
| 2005/0027457 | A1 | * | 2/2005 | Mandell et al. ............... 702/19 |

FOREIGN PATENT DOCUMENTS

| EP | 0 982 401 A1 | | 3/2000 |
| EP | 0 982 402 A1 | | 3/2000 |
| WO | WO 95/27787 A1 | * | 10/1995 |
| WO | WO 95/34308 A2 | * | 12/1995 |
| WO | WO 97/47312 | | 12/1997 |
| WO | WO 97/47312 A1 | | 12/1997 |
| WO | WO 97/49726 | | 12/1997 |
| WO | WO 97/49726 A1 | | 12/1997 |
| WO | WO 99/03987 | | 1/1999 |
| WO | WO 99/03987 A2 | * | 1/1999 |
| WO | WO 99/06569 A1 | * | 2/1999 |
| WO | WO 00/09701 | | 2/2000 |
| WO | WO 02/00882 | | 1/2002 |
| WO | WO 02/00882 A2 | | 1/2002 |

OTHER PUBLICATIONS

Langedijk et al. Enzyme-Linked Immunosorbent Assay Using a Virus . . . Journal Of Clinical Microbiology. Mar. 2001, vol. 39, No. 3, pp. 906-912.*
International Search Report, International Application No. PCT/NL01/00484, dated Mar. 22, 2002 (7 pages).
International Preliminary Examination Report, International Application No. PCT/NL01/00484, dated Jul. 9, 2002 (3 pages).
Feldman, Steven A., et al., "Identification of a Linear Heparin Binding Domain for Human Respiratory Syncytial Virus Attachment Glycoprotein G," 73(8) Journal of Virology 6610-17 (Aug. 1999).
Guichard, Gilles, et al., "Antigenic mimicry of natural L-peptides with retro-inverso-peptidomimetics," 91 Proc. Natl. Acad. Sci. USA 9765-69 (Oct. 1994).
Kishore, Ram, et al., "Interaction of the NH2-terminal Domain of Fibronectin with Heparin," 272(27) The Journal of Biological Chemistry 17078-85 (1997).
Mancheno, Jose M., et al., "Predictive Study of the Conformation of the Cytotoxic Protein α-Sarcin: A Structural Model to Explain α-Sarcin-Membrane Interaction," 172 J. Theor. Biol. 259-67 (1995).
Mayo, Kevin H., "Recent advances in the design and construction of synthetic peptides: for the love of basics or just for the technology of it," 18 Tibtech 212-17 (May 2000).
Moormann, R.J.M, "Recent Developments in Pig Vaccinology," Proceedings of the 14th IPVS Congress, Gologna, Italy, 25-29 (Jul. 7-10, 1996).
Yang, Xiaojing, et al., "Insights into specificity of cleavage and mechanism of cell entry from the crystal structure of the highly specific Aspergillus ribotoxin, restrictocin," 4(7) Structure 837-52 (1996).
PCT International Search Report, PCT/NL01/00484, dated Mar. 22. 2002.
Chang et al., HIV-1 Tat protein exits from cells via a leaderless secretory pathway and binds to extracellular matrix-associated heparan sulfate proteoglycans through its basic region, AIDS, 1997, pp. 1421-1431, vol. 11, No. 12.
Lindgren et al., Cell-penetrating peptides, Review, Mar. 2000, pp. 99-103, vol. 21.

* cited by examiner

*Primary Examiner*—Jeffrey E. Russel
(74) *Attorney, Agent, or Firm*—TraskBritt

(57) ABSTRACT

The invention relates to peptides derived from or similar to the E$^{ms}$ protein of pestiviruses for type-specific diagnosis of infection, for eliciting antibiotic activity, and for transport of substances into a cell. For these purposes, the invention provides, among other things, an isolated, synthetic or recombinant protein or pe

Fig. 3

```
csfv        ENARQGAARVTSWLGRQLSTAGKRLEGR--SKTWFGAYA     (SEQ ID NO:16)
bvdv        ESARQGTAKLTTWLGRQLKKLGKKLENK--SKTWFGAYA     (SEQ ID NO:85)
magainin    -----------GIGKFLHSAGKF--GK----AFVGEIMKS     (SEQ ID NO:24)
restrictocin ------DGNGKLIKGRTPIKFGKADCDRPPKHSQNGMK      (SEQ ID NO:86)
``` a b

Catching of biotinylated CSFVpeptide, blocking with BVDV peptide a

Catching of biotinylated CSFV peptide, blocking with BVDV peptide b

US 7,067,487 B2

TRANSPORT PEPTIDES SUCH AS C-TERMINAL E$^{RNS}$ PEPTIDE AND ANALOGUES THEREOF

CROSS-REFERENCE TO RELATED APPLICATION

This application is a continuation of International Application No. PCT/NL01/00484, filed Jun. 28, 2001, designating the United States of America, and published in English as WO 02/00882 A2 on Jan. 3, 2002, the contents of the entirety of which is incorporated herein by this reference.

TECHNICAL FIELD

The invention relates to transport peptides, for example, derived from the E$^{ms}$ protein of pestiviruses for type-specific diagnosis of infection, for eliciting antibiotic activity and for transport of substances into a cell.

BACKGROUND

Hog cholera virus or classical swine fever virus (CSFV), bovine viral diarrhea virus (BVDV), and border disease virus (BDV) belong to the genus *Pestivirus* of the Flaviviridae family. CSFV is restricted to swine, while BVDV and BDV have been, isolated from several species such as cattle, swine, sheep, deer, and giraffes. Although pigs can be infected by all of these pestiviruses, only CSFV induces severe, often fatal, disease. The disease is characterized by fever and, for instance, leukopenia and can run an acute, chronic, or subclinical course. Although effective live-attenuated vaccines are available, pigs are not vaccinated against CSFV in the European Union (EU) because vaccinated and infected pigs are serologically indistinguishable. Outbreaks of CSF in the EU are controlled by eradication of all pigs from infected farms and farms in the vicinity. Because of this strategy, more than 10 million pigs had to be killed and destroyed during the 1997–1998 CSF epizootic in the Netherlands, costing more than $2 billion. It is for this reason that a great demand exists for a marker vaccine that provides protective immunity and induces an antibody response in the vaccinated pigs that can be distinguished from the antibody response caused by a natural CSFV infection.

Like other members of the family, pestiviruses are plus-stranded RNA viruses whose genome comprises one long open reading frame. Translation into a hypothetical polyprotein is accompanied by processing into mature proteins. The structural proteins include a nucleocapsid protein C and three envelope glycoproteins E$^{ms}$, E1 and E2. The envelope proteins E$^{ms}$ and E2 are able to induce neutralizing antibodies. Glycoprotein E2 is the most immunogenic protein of pestiviruses and elicits high titers of neutralizing antibodies after infection. Vaccination of target animals with E2 has shown to give complete protection against a lethal homologous challenge. When E2 is used for vaccination, serological diagnosis of a natural pestivirus infection has to be performed with an immunogenic/antigenic protein other than E2 that is present in the infectious pestivirus. For this purpose, the E$^{ms}$ glycoprotein can be used as an antigen in a diagnostic test. A population that is vaccinated with the E2 glycoprotein can still be tested serologically for pestivirus infection with a diagnostic test based on the E$^{ms}$ antigen. A serological test based on E$^{ms}$ can distinguish E$^{ms}$ antibody-positive sera from animals infected with the virus and E$^{ms}$ antibody-negative sera from uninfected animals. This is called the marker vaccine approach. Of course, these marker vaccines depend on sensitive tests and, in the case of CSFV, the test also has to be very specific because pigs can be infected with the other pestiviruses BVDV and BDV. Because BVDV and BDV do not cause (severe) clinical symptoms in pigs and the animals are not vaccinated for these viruses, the diagnostic test for a CSFV marker vaccine should only detect CSFV antibodies and no other pestivirus antibodies.

Serological tests based on the complete E$^{ms}$ protein have been developed previously but are not always satisfactory in that they are not specific enough in that they cannot discriminate sufficiently between infections with different pestivirus species or are not sensitive enough to detect early infections with a pestivirus.

In one embodiment, the invention provides a so-called transport peptide module, herein also called "movin." In principle, we found that most linear peptides of 10 to 18 residues long which have >40% arginines (R) or lysines (K) are capable of functioning as such a transport peptide module to which cargo can be attached. Such a transport peptide module preferably should not, or only to a small extent, contain negatively charged amino acids such as aspartic acid (D) or glutamic acid (E). Preferred peptide modules are identified herein with full sequence, such as, for example, in Tables 4, 5, and 9 to 11, or retro-inverso variants thereof.

Variations in amino acid sequence are well tolerated, at least from the viewpoint of translocation as activity. As a rule of thumb, it can be said that related sequences have at least 30–50% homology, preferably at least 70% homology, and most preferably at least 85% homology, to those displayed in these tables, which allows identifying further relevant sequences present in nature or capable of being synthesized.

Substitutions in the amino acid sequence of a transport peptide module can be applied to increase the translocation (transport) activity. An optimized transport peptide module can, for example, be synthesized according to retro-inverso peptide chemistry, in which the sequence is reversed and D-amino acids are used instead of L-amino acids. Transport peptides derived from the herein-indicated positions of the E$^{ms}$ peptide, L3 loop peptides or human respiratory syncytial virus protein G (HRSV-G) peptides, and peptide mimics or peptoides derived thereof were able to bind surface glycosaminoglycans like heparin. Therefore, finding that a peptide belongs to the group of linear heparin-binding peptides or is capable of binding related glycosaminoglycans can be used as a prediction that they likely also can function as transport peptides. However, heparin binding is not a prerequisite for a peptide being a transport peptide.

To check if the presence of heparin on the surface of the cell influenced the efficiency of translocation, it was tested whether heparin-binding peptides also translocated into mutant cells which were glycosaminoglycan deficient (cell lines pgsA-745 and pgsD-677). Titrations of all heparin-binding peptides on the different cells showed that peptides translocated with the same efficiency/activity into heparin-containing cells and in the mutant cells without heparin (data not shown). Thus, heparin-binding peptides have translocation activity, and binding of the peptides to heparin obviously does not block the peptide from penetrating the plasma membrane. Likely, the peptides have a high on/off rate for heparin, and the high affinity for phospholipids directs the peptides to the membrane and ultimately into the cell. On the other hand, heparin binding, albeit being predictive, does not seem to be a prerequisite for efficient translocation of the peptides.

The invention further provides a method for translocating a compound over a membrane of a cell, an epithelial layer, mucus layer, blood-brain barrier or skin comprising providing the compound with a transport peptide module according to the invention and contacting it with a cell. Such compounds, herein also called cargo, can be large; successful translocation of compounds up to 600 kD has been demonstrated and it is expected that even larger compounds may be translocated. From the perspective of speed of translocation in relation to the usefulness of the compound, compounds of preferred molecular weight are those of 60 to 500 kD and even more preferred are those of 120 to 300 kD. Compounds can also be of a varied nature. For example, it is possible to link macromolecules such as nucleotides, polypeptides, drugs such as antiviral, antimicrobial or anti-inflammatory drugs, and the like to a module as provided herein for successful translocation of such a compound. Topical application of such a compound, e.g., as a pharmaceutical composition, is specifically provided. A module as provided herein has excellent capacity to penetrate to the upper layers of the skin. Typical applications include further use of a labile linker such as a thioester or a O(C=O)CH$_2$NRC(=O)CH$_2$NHCH$_2$ (C=O) SCys linker. For use of a transport peptide module according to the invention, drugs or macromolecules are typically covalently coupled to the peptide, examples of which are cyclosporine A, acyclovir, and terbenafine coupled with a module according to the invention.

This invention also provides, among others, peptide-based diagnostics in connection with diseases caused by pestivirus infections. Antigenic peptides as provided herein and useful for diagnostics can surprisingly also be used otherwise, such as antibacterial or transport peptides. Because in one embodiment the transport peptide module is a fragment derived of the E$^{rns}$ protein, it can be used for diagnosis of pestivirus infections when a marker vaccine is used that is based on E2, another pestivirus surface protein. Due to its unique biochemical character, a peptide as provided herein has the ability to permeate and kill microorganisms and has the ability to translocate itself and a coupled cargo across a cell membrane and epithelium barrier.

In a preferred embodiment, the invention provides a thus far unidentified small, independently folding protein (peptide) module related to modules present at the C-terminal end of pestivirus E$^{rns}$, at the L3 loop of secreted cytotoxic Rnases that preferably belong to the group of type II ribotoxins such as alpha-sarcin, restrictocin, mitogillin, toxin Asp fI, clavin or gigantin, in a heparin-binding peptide, in a DNA/RNA-binding peptide, in HRSV-G protein, and its use as a transport peptide. Previously, the region responsible for translocation of alpha-sarcin was thought to be located in a hydrophobic stretch, located away from the L3 loop (Mancheno et al., Biophys. J. 68, 2387–2395, 1995). In a preferred embodiment, the invention provides an isolated, synthetic or recombinant protein module or functional equivalent thereof comprising an amino acid sequence that is at least 85% identical to any of the sequences shown in Tables 1–4 and 9–11, e.g., to an amino acid sequence of a peptide located from about amino acid position 194 to 220 in a pestiviral E$^{rns}$ protein and/or that is at least 70% identical to an L3 loop sequence such as shown in Table 5.

Such transport peptide modules can be prepared synthetically with normal peptide synthesis or coupling techniques as described herein, starting from individual amino acids or by coupling or linking smaller peptides of relevant sequence to another or by cleaving off from larger peptides. When desired, nonconventional amino acids can be used, such as D-amino acids or others that normally do not occur in natural proteins. Peptides can also be prepared via recombinant DNA techniques via transcription and translation from recombinant nucleic acid encoding such a peptide or protein module, be it linked to, for example, a fusion protein or specific target molecule such as a desired binding molecule derived from an antibody or protein ligand or receptor-binding molecule, and so on. For example, we have successfully expressed a fusion protein of a transport peptide and Green Fluorescent protein in A72 cells. The Green Fluorescent protein showed the same cellular localization as the biotinylated transport peptide in the nucleoli and around the nucleus. This is in contrast to normally expressed Green Fluorescent protein, which was distributed evenly over the cell (data not shown).

In a preferred embodiment, the invention provides a transport peptide module or functional part thereof wherein at least the functional part of the peptide comprises a reversed amino acid sequence to one of a sequence given in claims 1 to 6 and wherein D-amino acids are used instead of L-amino acids. Reversing the sequence and using the D-amino acids instead enhances translocation activity, allowing improved use for, for example, transport of macromolecules or drugs through cell membrane barriers into cells.

In a preferred embodiment as explained herein, the invention provides a module which is functional as a transport peptide module, also when cargo is attached, wherein the peptide is located from about amino acid position 191 to 222, or from about 194 to 227, or from about 191 to 227, or from about amino acid position 176 to about 220, 222, or 227 in the case of the pestiviral E$^{rns}$ protein or residues 51–91 or 59–88 or from 62–88 or from 62–74, in the case of the L3 loop protein, or from about amino acid position 187 to 223 in a respiratory syncytial virus G-protein. Also, in HRSV type B, a similar region was detected from position 149 to 160 in protein G. These amino acid positions and their numbering are, of course, relative to known sequences as, for example, shown in the figures herein wherein alignments of various pestiviral sequences are shown, which, of course, allows, for example, for alignment with yet unknown pestiviral sequences and allows alignment with ribotoxin L3 loop sequences. As a rule of thumb, it can be said that related sequences have at least 30–50% homology, preferably at least 70% homology, most preferably at least 85% homology, which allows identifying further relevant sequences present in nature or capable of being synthesized. As examples herein, modules are described wherein the peptide comprises the amino acid sequence RQGAARVTSWLGKQLRIAGKRLEGRSK (SEQ ID NO:1); RQGTAKLTTWLGKQLGILGKKLENKSK (SEQ ID NO:2); RVGTAKLTTWLGKQLGILGKKLENKTK (SEQ ID NO:3); RQGAAKLTSWLGKQLGIMGKKLEH-KSK (SEQ ID NO:4); GNGKLIKGRTPIKFGKADCDRP-PKHSQNGMGK (SEQ ID NO:5); GDGKLIPGRTPIKF-GKSDCDRPPKHSKDGNGK (SEQ ID NO:6); GEGKILKGRTPIKFGKSDCDRPPKHSKDGNGK (SEQ ID NO:7); GDGKILKGRTPIKWGNSDCDRPPKHS-KNGDGK (SEQ ID NO: 8); KRIPNKKPGKK (SEQ ID NO:9); KTIPSNKPKKK (SEQ ID NO:10); KPRSKNPP-KKPK (SEQ ID NO:11) or a functional part thereof. However, variations can be introduced, for example, by increasing the positive charge of the peptide, preferably at positions that optimize the amphipathic nature of the peptide, but not necessarily. Another example is changing several or all L-amino acids to D-amino acids to reduce possible protease sensitivity. The translocation activity of the E$^{rns}$ peptide was further improved by substitution of the 2 lysines and the glutaminic acid by arginines. In a preferred embodiment, a retro-inverso variant of an above-identified peptide module is provided; such a retro-inverso peptide with an inversed sequence and D-amino acids replacing L-amino acids comprises even higher translocation activity.

Of course, the invention also provides a recombinant nucleic acid encoding a module according to the invention, for example, to provide for a proteinaceous substance provided with a module according to the invention, for example, provided with a targeting means.

The invention in one aspect also relates to the design of an antigenic substance, preferably peptide-based, corresponding to the protein module in the $E^{rns}$ protein of Pestiviruses or a L3 loop of ribotoxin H can be used as a basis for, e.g., diagnostics tests, antibacterial or transporter peptides. For example, in one embodiment, the invention provides a method for inducing an antibody comprising administering a module or a substance according to the invention to a host capable of forming antibodies. Antibodies can be induced classically by, for example, immunizing an animal with the antigenic substance, or via more modern techniques, such as phage display, whereby so-called synthetic antibodies are produced. Be it synthetic or classical (mono- or polyclonal), the invention provides an antibody specifically directed against a module according to the invention.

With the pestivirus-derived module and/or the antibody as provided herein, the invention provides a method for detecting the presence or absence of an antibody directed against a pestivirus in a sample comprising contacting the sample with a module or a substance according to the invention, the method preferably further comprising detecting the presence or absence of an antibody bound to the module or substance. Also provided is a method further comprising contacting the sample with the module or substance in the presence of a competing antibody directed against the module and detecting the presence or absence of competing antibody bound to the module or substance. Herewith, the invention provides use of a method according to the invention for differentiating at least one animal from at least another animal. The invention thus provides a test which is based on a small fragment of the $E^{rns}$ protein. Sequence analysis and homology modeling was used for pestivirus $E^{rns}$ to identify a region that can be used for the design of antigenic substances and resulted in the identification of a small independently folding protein module which, in its native state, is exposed on the protein surface of the complete $E^{rns}$ protein and can be used to design antigenic substances which are comparable or superior to the complete protein.

In a further embodiment, the invention not only provides a peptide that behaves as a superior antigen in the $E^{rns}$ peptide-ELISA but one that has additional characteristics that are very interesting and useful. Due to its unique biochemical nature, a peptide as provided herein, for example, corresponding to the $E^{rns}$ C-terminal domain or to a L3 loop in a ribotoxin, is able to interact with a cell membrane and destabilize the membrane.

The invention further provides a method for translocating a compound over a membrane of a cell, an epithelial layer, mucus layer, blood-brain barrier or skin comprising providing the compound with a module or substance or transport peptide module according to the invention and contacting it with a cell, and, furthermore, it provides a method for eliciting antibiotic activity to a microorganism comprising contacting the microorganism with the module or substance.

Herein, it is shown that such an $E^{rns}$ peptide or protein module as provided herein has antibacterial activity for, for example, gram-negative bacteria (*E. Coli*) and an L3 loop or $E^{rns}$ peptide and it has translocation activity for, for example, eukaryotic cell membranes. A biological membrane is a very efficient barrier that protects the micromilieu of cells or intracellular compartments from the outside milieu. In order to interfere directly with biological processes inside the cell, it is necessary that pharmaceuticals cross the lipid bilayer to block/bind their targets. Many promising, potential therapeutics (hydrophilic organic molecules, peptides, proteins or genes) are ineffective because the cell membrane forms an insurmountable barrier. However, several peptides have been discovered recently that can solve this problem because they are able to translocate over the lipid bilayer and are also able to transport a diverse set of cargos inside the cell.

Interactions of pore-forming peptides with model and artificial membranes have been studied extensively the last three decades. Several families of membrane destabilizing peptides with antitumor, haemolytic, antibacterial activity or a combination have been found. Many of these peptides form amphipathic helices with a hydrophobic face and a positive charged face that organize and aggregate on the membrane surface and destabilize the membrane. Their mode of action has some resemblance with the recently discovered transport peptides (Matsuzaki et al., Biochem. Biophys. Acta. 1376: 391–400, 1998; Lindgren et al., Trends Pharmacol. SCI 21: 99–103, 2000). The invention now provides a pharmaceutical composition comprising a module or substance according to the invention useful for several purposes. For example, the invention provides use of a module or a substance according to the invention for the preparation of a pharmaceutical composition capable of membrane translocation (a transport peptide), for the preparation of a pharmaceutical composition capable of eliciting antibiotic activity (an antibiotic), or for the preparation of a pharmaceutical composition capable of inducing antibodies (a vaccine) upon administration to a host.

The invention is further explained in the detailed description described herein without limiting it thereto.

BRIEF DESCRIPTION OF THE DRAWINGS

FIG. 3. Sequence alignment of pestivirus $E^{rns}$ C-terminal domains with magainin and the L3 loop of restrictocin. Residues within one distance unit from magainin are boxed. Units are defined in structural distance table in the magalign package of DNASTAR, Inc. The Structural table scores for residues that are chemically and spatially similar. All identities score a value of 6. Mismatches score less than identities. The Structural table is designed for use with the Jotun-Hein method.

FIGS. 6A and 6B. Reactivity of several panels of sera in the CSFV 1p-peptide ELISA as described in the test procedure. Negative field serum samples (n=96) were randomly obtained from slaughtered adult pigs and were all tested negative in standard pestivirus ELISA. Pestivirus-positive but CSFV-negative serum samples (n=96) were randomly obtained from slaughtered adult pigs. CSFV-positive field serum samples were obtained (n=95) from an infected farm (VR) that was infected during the CSF epizootic in the Netherlands in 1997–1998.

DETAILED DESCRIPTION

Figure 1:
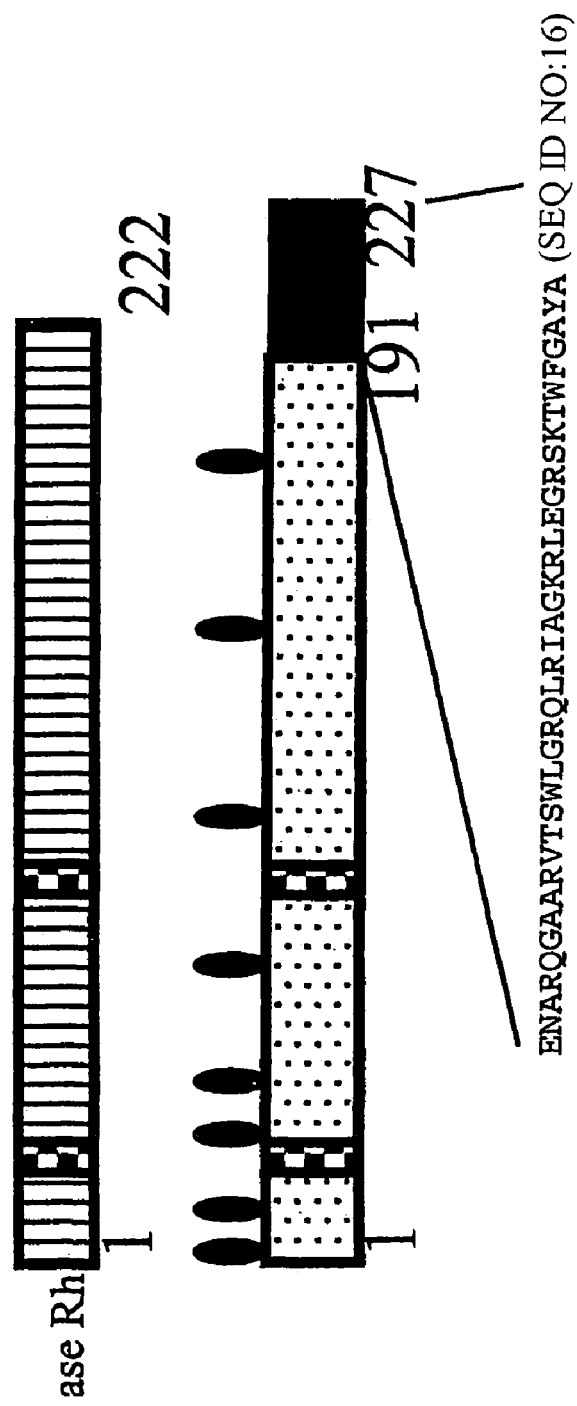
FIG. 1. Schematic representation of alignment of pestivirus $E^{rns}$ with RNase Rh which indicates the modular organization of $E^{rns}$. $E^{rns}$ consists of an RNase domain (dotted) and a C-terminal membrane-active domain (filled black). The C-terminal domain (residues 191–227) which shows resemblance to the L3 loop of cytotoxic RNases is described in this invention. RNase-active site domains are shown as checkered boxes. Potential glycosylation sites are shown as ellipses.

For diagnostics, the invention provides a peptide comprising an amino acid sequence derived from E$^{ms}$ of a pestivirus, wherein the amino acid sequence has, for example, a length of 37 amino acid residues corresponding to the C-terminus of E$^{ms}$, which is located C-terminal to the RNase domain. Preferably, the amino acid sequence comprises at least the amino acid residues 191–227 of Pestivirus E$^{ms}$ and has at most 4 amino acid differences therewith. Preferably, the pestivirus E$^{ms}$ peptide is selected from the group consisting of Classical Swine Fever Virus (CSFV), strain Alfort 187, BVDV-1 strain M96751, BVDV-2, or BDV, strain X818. The amino acid sequence preferably comprises a member selected from the group consisting of:

TABLE 1

| | |
|---|---|
| CSFV | ENARQGAARVTSWLGRQLRIAGKRLEGRSKTW (SEQ ID NO:12) |
| BVDV-1 | EGARQGTAKLTTWLGKQLGILGKKLENKSKTW (SEQ ID NO:13) |
| BVDV-2 | EGARVGTAKLTTWLGKQLGILGKKLENKTKAW (SEQ ID NO:14) |
| BDV | ENARQGAAKLTSWLGKQLGIMGKKLEHKSKTW. (SEQ ID NO:15) |

More preferably, a member selected from the group consisting of:

TABLE 2

| | | |
|---|---|---|
| CSFV | ENARQGAARVTSWLGRQLRIAGKRLEGRSKTWFGAYA | (SEQ ID NO:16) |
| BXTDV-1 | EGARQGTAKLTTWLGKQLGILGKKLENKSKTWFGAYA | (SEQ ID NO:17) |
| BVDV-2 | EGARVGTAKLTTWLGKQLGILGKKLENKTKAWFGAHA | (SEQ ID NO:18) |
| BDV | ENARQGAAKLTSWLGKQLGIMGKKLEHKSKTWFGANA | (SEQ ID NO:19) |

Such as a member selected from the group consisting of:

TABLE 3

| | | |
|---|---|---|
| CSFV | DTALYLVDGMTNTIENARQGAARVTSWLGRQLRIAGKRLEGRSKTWFGAYA | (SEQ ID NO:20) |
| BVDV-1 | DTTLYLVDGLTNSLEGARQGTAKLTTWLGKQLGILGKKLENKSKTWFGAYA | (SEQ ID NO:21) |
| BVDV-2 | ETAIQLLDGATNTIEGARVGTAKLTTWLGKQLGILGKKLENKTKAWFGAHA | (SEQ ID NO:22) |
| BDV | DTALYVVDGVTNTVENARQGAAKLTSWLGKQLGIMGKKTLEHKSKTWFGANA | (SEQ ID NO:23). |

It is preferable that the peptide is capable of adopting the tertiary structure of its counterpart in the corresponding E$^{ms}$ protein when it relates to an antigenic substance, or a precursor thereof, which allows discrimination between or identification of different pestivirus types or subtypes, or allows discrimination between or identification of antibodies against different pestivirus types or subtypes, which antigenic substance or precursor thereof comprises a peptide as defined herein.

A peptide, antigenic substance or precursor thereof as defined herein may be used in diagnosis of Pestivirus infections. This invention also provides a diagnostic test kit for the detection of Pestivirus, or antibodies against Pestivirus types or subtypes, which test kit comprises a peptide, antigenic substance or precursor thereof as defined herein, together with suitable means for detection. The test kit preferably provides for an enzyme-linked immunosorbent assay.

The invention also provides a method for the detection of (antibodies against) Pestivirus comprising contacting a sample of a body fluid with a peptide, antigenic substance or precursor thereof as defined herein, in a manner such that a complex comprising the peptide, antigenic substance or precursor, and an antibody directed against the peptide, substance or precursor can be formed, followed by detection of the complex.

Furthermore, the invention provides a pharmaceutical composition or vaccine for the prophylaxis of Pestivirus infections comprising a peptide, antigenic substance or precursor thereof as defined herein, together with a suitable adjuvant or excipient for administration to a mammal. The invention also provides a method for the prophylaxis of Pestivirus infections comprising administering to a mammal a composition as defined above, in an amount sufficient to elicit an immune response against Pestivirus.

Furthermore, the invention provides a peptidomimeticum that mimics a peptide as defined herein.

Another aspect of this invention is a method for inducing antibodies against Pestivirus types or subtypes comprising administering to a mammalian host an antigenic substance or precursor thereof as defined herein, together with a suitable adjuvant, and harvesting resulting antibodies or antibody-producing cells from the mammalian host.

An antibody directed against a type or subtype of Pestivirus obtainable by the above method is also part of the invention. Preferably, the antibody is a monoclonal antibody.

In another aspect, the invention provides a diagnostic test kit for the detection of or the discrimination between (antibodies against) subtypes or types of Pestivirus comprising the above antibody and suitable means for detection.

For antibacterial and transport activity, the invention provides a similar amino acid sequence as listed in Tables 1 and 2. Systematic analysis showed that shorter peptides comprising $E^{rns}$ amino acids 194–220 had higher transport activity and lower hemolytic activity. This amino acid sequence preferably comprises a member selected from the group consisting of:

TABLE 4

| | |
|---|---|
| CSFV | RQGAARVTSWLQRQLRIAGKRLEGRSK (SEQ ID NO:1) |
| BVDV-1 | RQGTAKLTTWLGKQLGILGKKLENKSK (SEQ ID NO:2) |
| BVDV-2 | RVGTAKLTTWLGKQLGILGKKLENKTK (SEQ ID NO:3) |
| BDV | RQGAAKLTSWLGKQLGIMGKKLEHKSK (SEQ ID NO:4) | or those presented in Table 5 relating to the L3 loop of ribosome-inactivating proteins.

Most peptides that have been used in serology represent continuous epitopes. It is impossible to detect antibodies against complex discontinuous epitopes using small linear peptides and it is difficult to predict discontinuous epitopes based on the amino acid sequence of a protein. In addition, the antigenic surface of large globular proteins cannot be mimicked accurately with a small linear peptide. We solved this problem by predicting an independently folding region in the $E^{rns}$ protein of pestiviruses that adopts a stable tertiary structure while retaining its antigenicity. This prediction is crucial for the correct design of a useful antigen. Two stretches of Pestivirus $E^{rns}$ show sequence homology with ribonuclease Rh (RNase Rh), a new class of microbial ribonuclease of *Rhizopus niveus*, a member of the $T_2/S$ RNase superfamily. A typical feature for this type of RNase is the low base specificity and the large molecular weight. The crystal structure of RNase Rh has been determined (Kurihara et al., J. Mol. Biol. 255: 310–320, 1996) and the three-dimensional (3D) structure confirmed that both stretches with sequence homology to $E^{rns}$ constitute the active site of the RNase. Apart from the two stretches of sequence homology, further homology in the rest of the protein was not apparent.

Despite a low sequence homology, we were able to construct an alignment using different types of scoring matrices and multiple sequence alignment of a large set of RNase sequences. A satisfactory alignment was not possible using alignment software with any parameter setting. Therefore, a part of the alignment was edited manually. For parts with low sequence homology, the alignment was guided by secondary structure prediction of the PHD software (Rost, B. and Sander, C., 1992, Nature, 360:540).

Figure 2:
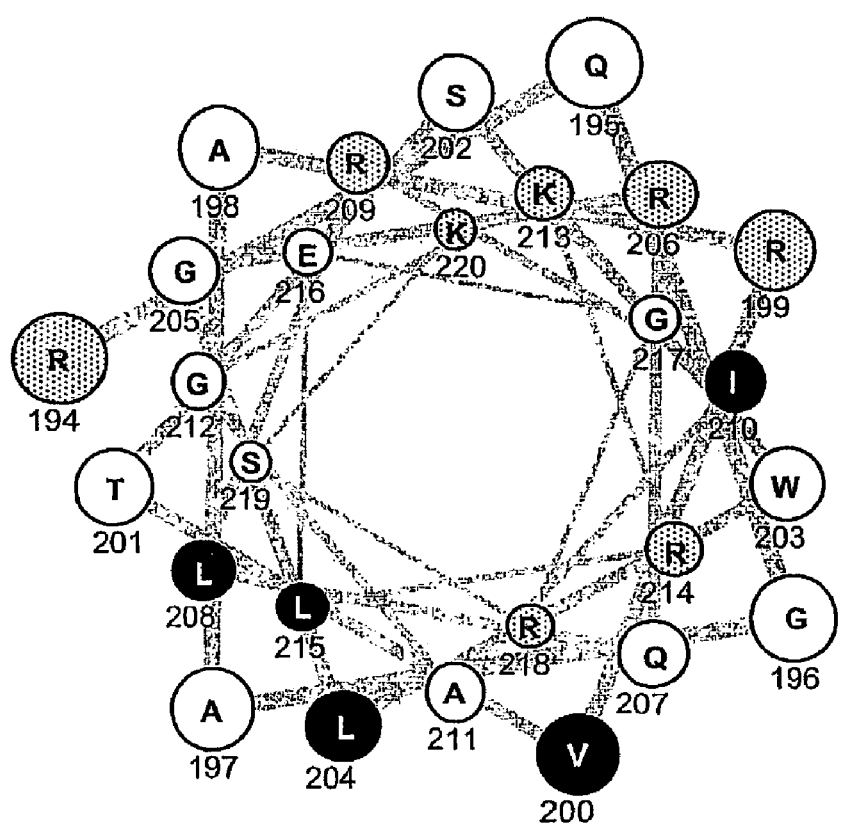
FIG. 2. Helical wheel representation of residues 194–220 of CSFV $E^{rns}$.
Figure 4:
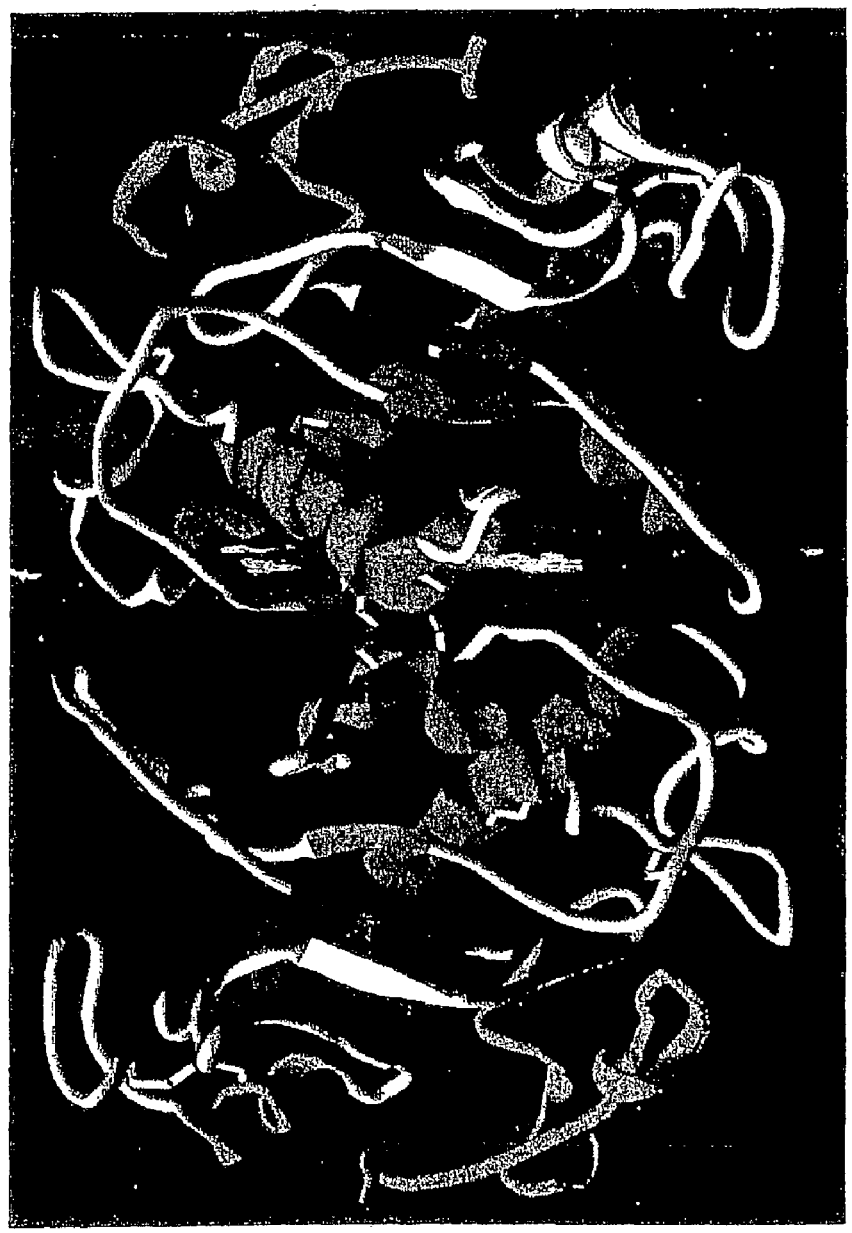
FIG. 4. Crystal structure of RNAse Rh.

After inspection of the multiple sequence alignment, some major dissimilarities between the sequences of pestivirus $E^{rns}$ and the other RNases can be observed. Compared with sequences of the other RNases, the pestivirus sequences have a truncation at the N-terminus, large insertions after residues 83 and 135 and an elongated and very dissimilar C-terminus. The 37 C-terminal residues could not be aligned with the other RNases. Other characteristics of the C-terminus are the high number of positive charges and a high score for amphipathic helicity. A helical wheel representation of residues 191–221 shows an amphipathic helix with a hydrophobic face and a positively charged face (FIG. 2). The only three residues that may not correspond with the perfect amphipaticity are Ile210, Arg214 and Arg218. Although no obvious domains were found with software like SMART (Schultz et al., PNAS 95: 5857–5864, 1998), this C-terminal region, which is separate from the RNase domain according to the alignment, with its typical secondary structure can now be considered as a separate domain or module. Such a positively charged domain in an RNase molecule is not unique for $E^{rns}$ but has also been observed in type II ribotoxins, another class of RNases. This class of RNases comprises extracellular cytotoxins that hydrolyze the large ribosomal RNA (22) and are able to translocate across phospholipid bilayers (23). Although ribotoxins are known to enter cells, it is not known which region of the protein is responsible for translocation. The type II ribotoxins like alpha-sarcin and restrictocin contain a large inserted L3 loop (residues 53–91) compared with other RNases of the T1 superfamily (24, 25). This loop has structural similarity (but no sequence similarity) to loops found in lectin sugar-binding domains and may be responsible for the ribotoxin's ability to bind to the cell surface (24). The C-terminal domain of $E^{rns}$ has approximately the same length and contains similar sequence motifs as the ribotoxin II L3 loop (FIG. 3). Although the sequence similarity between the ribotoxin L3 loop and the C-terminus of $E^{rns}$ is low (FIG. 3), it is higher than the sequence similarity between L3 and the structurally similar lectin-binding domains (24). Although the ribotoxin L3 loop is also positively charged, it has no apparent amphipathic character. Another interesting homology of the $E^{rns}$ C-terminal region is with the membrane interacting peptide magainin. The center of the $E^{rns}$ peptide has high sequence homology with the N-terminal half of magainin (FIG. 3). This homology is even higher compared to the homology of magainin with other pore-forming peptides that have been described (26)

The (overall) 3D structure of $E^{rns}$ is similar to RNase Rh except for the C-terminal region, which is surprisingly similar to loop L3 of restrictocin or other ribotoxin II proteins. (This protein module likely folds independently, is metastable and can change to an alpha helical structure when it binds to the cell membrane.) The 3D structure of the C-terminal domain is not very important because of its spatial independence from the RNase domain.

With the aid of a modular structure, it is possible to define antigenic regions on the surface of the protein which can be mimicked by single linear peptides. The domain corresponding to the C-terminal 37 residues (191–227) is the best candidate because of its location on the outer rim on the surface of the $E^{rns}$ dimer; it forms a small functional domain which folds independently from the rest of the protein and it is not masked by any potential carbohydrate.

Development ELISA

The invention provides an antigenic and, in essence, proteinaceous substance for discrimination of infected animals with different types of pestiviruses from animals vaccinated with a subunit vaccine that does not contain the $E^{ms}$ peptide and infected animals. The antigenic substance is a peptide that corresponds to a C-terminal amino acid sequence of Pestivirus $E^{ms}$ which does not align with RNase Rh but with an L3 loop of a ribotoxin and folds independently from the rest of the protein.

An antigenic substance according to this invention is to be interpreted as any peptide-like or peptide-based substance (e.g., a protein module as provided herein optionally linked to another group such as a peptide or protein) capable of inducing an immune response against pestivirus or being recognized by serum-containing antibodies against a pestivirus. Precursors of such antigenic substances are, for example, comparable peptide-like or peptide-based substances which are not immunogenic themselves but need, for instance, to be coupled to a carrier to be able to induce an immune response or to be recognized. Peptide-based or peptide-like substances are intended to include anything with the function of the peptides according to the present invention. This means that these substances may be peptides themselves in which a number of amino acid residues have been replaced or modified. It also means that they may be fusion proteins, for instance, designed to present the amino acid sequence of the peptides of the invention on their surface. The definition also includes peptidomimetics and anti-idiotype antibodies derived from the peptides according to the invention.

In a preferred embodiment, the invention provides peptides that can be used in diagnostic assays for detection of antibodies directed against specific pestivirus types (CSFV, BDV, BVDV-I, BVDV-II).

The provision of the protein module, the independently folding region of $E^{ms}$, relates to all types of pestiviruses and beyond. As a consequence, the invention is not limited to the peptides specifically disclosed herein, but extends to analogous peptides and their derivatives in all types of pestiviruses and all subtypes of these viruses and to homologues of the L3 loop of (ribosome inactivating) ribotoxin II proteins. Preferred peptides to be used according to the invention comprise at least antigenic parts of the peptides given in Table 2 or derivatives thereof, their length being from about 27 residues up to about 51 residues or transport peptides according to any one of Tables 1–5.

We have evaluated the applicability of the peptides in diagnostics by the development of different diagnostic assays: indirect ELISAs in which the antigen is recognized in solid phase and an indirect ELISA in which the antigen is recognized in liquid phase. Other diagnostic assays can, of course, be easily designed by the man skilled in the art. These may, of course, be provided in any suitable format.

Assays can be performed in solution and on solid phases. They can be performed using any kind of label, such as enzymes, solid particles, such as metal sols, or other sols, latex particles, dyes, fluorescent substances or radioactive materials. They even may be performed without labels, as can be done by agglutination assays. The peptides can be used to detect antibodies in, for instance, a fluid from a mammal, such as blood, serum, urine, and milk. Usually, the antibody is bound by a peptide, module or substance according to the invention, which may be present on a solid phase or in a liquid phase. Afterwards, the complex of peptide and antibody may be detected by a labeled reagent, which can be a labeled antibody directed against the host's (such as swine, bovine or sheep) antibodies.

According to the invention, the peptides can also be used to obtain antibodies which are specific for Pestivirus types and/or subtypes. The peptides are administered to a mammal, usually a rodent, in an immunogenic form, and after one or more booster administrations, the serum from the animal is harvested and antibodies can be purified therefrom.

Alternatively, the spleen of such animals may be removed to obtain antibody-producing cells. These can be changed, by fusion or transformation, into cell lines producing monoclonal antibodies. Assays based on (monoclonal) antibody-directed Pestivirus and induced by the peptides according to the invention are, therefore, also a part of the invention.

The peptides according to the invention can, of course, also be used in vaccines to prevent infection with Pestivirus. They may be used in conjunction with other antigens to elicit an immune response against Pestivirus. Usually, the peptide has to be coupled to a carrier to be presented in an immunogenic form before administration to a host. Other ways of rendering a peptide sufficiently immunogenic are known to the person skilled in the art. Adjuvants are usually added to vaccines to boost the immune response in a more a specific manner.

Antibacterial and Transport Peptide

The invention further provides a membrane-active peptide or module or substance which can be used as an antibiotic and can be used as a transport peptide which is, for example, capable to carry cargos across the cell membrane. For coupling of cargo such as macromolecules, such as drugs, use is preferably made of a free hydroxyl group when available on the compound to be bound.

To use transport peptides as a drug-delivery system, these peptides can be linked to drugs via linkers. From the side of the drug or compound, for instance, cyclosporine A, acyclovir, or terbenafine, a functional group like the hydroxyl group can be used to couple a linking group via an ester bond. In the linking group, a function like a secondary amine (—NH—) can be inserted, which, by its orientation, catalyzes the cleavage of the ester bond with the drug and subsequently releases the original drug. An example of such a linker is: (drug)-O—CO—CH$_2$—NR—CO—CH$_2$—NH—CH$_2$—CO-link2-(transport peptide).

The transport peptide can be coupled to this linker by a second linker (link2) using different chemistries. For instance, ethylenediamine can be coupled to the free carboxylic acid of the first linker. Subsequently, the resulting amino group can be coupled to a bromoacetic acid and this bromoacetyl group can react in high yield with, for instance, the free —SH group of a cysteine in the transporter peptide. Alternatively, the transport peptide can also be coupled directly to the labile linker via, for instance, a free amino group from the transport peptide.

Substituents in the linker on the different groups, like the group R on the tertiary amine, can help to regulate further the stability of the ester. Alternatively, thioesters can also be used as an even more labile linking group.

Alternative strategies can be used for the coupling of the transporter peptide to compounds that have no easily accessible hydroxyl group available. In the case of terbenafine, an ethynyletheen function can, for example, be used for the addition of the free —SH group in the linker to form for instance: (drug) —S— (CH$_2$) n-NR—CO—CH$_2$—NH—

CH₂—CO-link2- (transport peptide). This conjugate can easily be cleaved under basic conditions (internal base is present as secondary NH-group), releasing the original drug, here, in the example, terbenafine. The membrane-active peptide is similar to the described antigenic peptide which corresponds to a C-terminal amino acid sequence of Pestivirus $E^{ms}$ which does not align with RNase Rh but does align with magainin and, to some extent, with the L3 loop of ribotoxins and folds independently from the rest of the protein. The L3 loop peptides are specifically membrane-active peptides according to the invention as well. A membrane-active substance according to this invention comprises, for example, a peptide-like or peptide-based substance capable of inducing leakage of a bacterial membrane or disturbance of a eukaryotic cell membrane without leakage. Peptide-based or peptide-like substances are intended to include anything with the function of the peptides according to the present invention. This means that these substances may be peptides themselves in which a number of amino acid residues have been replaced or modified. It also means that they may be fusion proteins, for instance, designed to modify the cell specificity of the peptide. Preferred peptides to be used according to the invention comprise at least the membrane-active part of the peptides given in Tables 4, 5 and 10. Derivatives with a higher translocation activity are listed in Table 9.

The invention relates to a set of pestivirus diagnostic assays, antibacterial peptide and transport peptide based on peptides corresponding to the C-terminal domain of pestivirus $E^{ms}$ or the L3 loop of ribotoxin type II proteins. Preferred regions used for peptide-based diagnostics are listed in Table 2 and preferred membrane-active peptides used for antibiotics or transport peptides are listed in Tables 4 or 5, and 9 to 11. However, they can, of course, be used interchangeably for their various uses. The length of the peptide to be used in a diagnostic assay or vaccine is conveniently the exact length of the domain (residues 191 to 227, 37 residues) but can, of course, be shorter or longer, as long as it does not essentially change in antigenic or immunogenic character. The maximum length of a suitable peptide (residues 177 to 227, 51 residues) can incorporate a 14-residue linker region between the RNase domain and the C-terminal domain. This linker region may be exposed in case of uncertainty of the exact spatial position of the C-terminal domain relative to the RNase domain and because of the conformational change of the C-terminal domain. For that reason, the linker region may be part of a large C-terminal antigenic site. The preferred minimum length of a suitable peptide to be used in a diagnostic assay or vaccine is the part of the C-terminal domain that forms an amphipathic helix. This is the part of the C-terminal domain without the 5 C-terminal hydrophobic residues (191 to 222, 32 residues).

The diagnostic assays based on the peptides can be used to determine antibody levels in blood, serum, milk or other body fluids.

The materials according to the invention can be used for incorporation in vaccines, for example, to provide for a carrier of the desired antigen-to-antigen presenting cells, or to present an antigen within the context of MHC (I or II) peptide presentation, or to provide for mucosal vaccination by providing translocation of a desired antigen over an epithelial (gut) layer. The peptide can also be used to transport various cargos in eukaryotic cells, as far as into the Golgi system or in the nucleus of cells. Such cargos can comprise protein or peptide material, PNA, RNA or DNA, drugs, secondary metabolites, and so on. Peptide mixtures could be used as well to provide for synergy in antibacterial activity, transportation or translocation.

EXAMPLES

Structure Analysis of Pestivirus $E^{ms}$

A detailed analysis of the primary structure and homology modeling of pestivirus $E^{ms}$ allowed the definition of antigenic regions on the surface of the protein which can be mimicked by single linear peptides. The C-terminal 37 residues (191–227) are the best candidates because of their location on the outer rim on the surface of $E^{ms}$ and because they fold independently from the rest of the protein as a subdomain and are not masked by any potential carbohydrate. The independent character of the C-terminus is also illustrated by the functional analysis of $E^{ms}$. $E^{ms}$ mutants have been made which are truncated from residue 168. In these mutants, the whole C-terminal part from residues 169 to 227 is missing. This mutant is still able to fold natively because the discontinuous active site is still intact and the mutant has wild-type RNase activity. Furthermore, the C-terminal 37 residues don't align with the other RNases but they do align with an L3 loop in ribotoxin type II proteins and with membrane-active peptides like magainins. These membrane-active peptides have a well-defined function, and for the magainins, it has been shown that they adopt helical conformations if they contact the cell membrane. We have demonstrated the membrane-active property of the $E^{ms}$ and/or L3. The membrane-active properties of the $E^{ms}$ peptide agree with the functionally independent nature of the subdomain. The location of this subdomain, the possibly independent folding of the sequence, the lack of potential glycosylation sites and its biological function make a peptide representing this region a suitable candidate to be used as an antigen/immunogen for immunoassays and vaccines. Furthermore, the biological activity of the $E^{ms}$ or the L3 peptide makes these peptides suitable candidates to be used as an antibacterial agent and/or a transport peptide.

ELISA Development

Peptide Synthesis

Peptides were selected from the C-terminal region (residues 191–227) of CSFV $E^{ms}$, strain Alfort 187, BVDV $E^{ms}$, strain M96751 and BDV $E^{ms}$, strain X818 and the L3 loop of restrictocin (residues 59–88; Lamy and Davies, NAR 19: 1001–1006, 1991) and magainin (Zasloff, PNAS 84: 5449–5453, 1987):

CSFV: acetyl-ENARQGAARV TSWLGRQLRI AGKRLEGRSK TWFGAYA-COOH (SEQ ID NO:16)
CSFV: biotin-ENARQGAARV TSWLGRQLRI AGKRLEGRSK TWFGAYA-COOH (SEQ ID NO:16)
BVDV: acetyl-EGARQGTAKL TTWLGKQLGI LGKKLENKSK TWFGAYA-COOH (SEQ ID NO:17)
BVDV: biotin-EGARQGTAKL TTWLGKQLGI LGKKLENKSK TWFGAYA-COOH (SEQ ID NO:17)
BDV: biotin-ENARQGAAKL TSWLGKQLGI MGKKLEHKSK TWFGANA-COOH (SEQ ID NO:19)
restrictocin: biotin-GNGKLIKGRTPIKFGKADCDRPP-KHSQNGMGK-NH₂ (SEQ ID NO:5)
magainin: biotin-GIGKFLHSAGKFGKAFVGEIMKS-NH₂ (SEQ ID NO:24)

Peptides were synthesized according to standard procedures on an Applied Biosystems 430A synthesizer using Fastmoc chemistry (Fields et al., Pept. Res. 4: 95–101, 1991). An extra CSFV and BVDV peptide were synthesized which were N-terminally biotinylated instead of acetylated.

Serum Samples

The following swine serum samples were incorporated in the study to evaluate the peptide ELISAs.

Negative field serum samples (n=96) were randomly obtained from slaughtered adult pigs. Sera were all tested negative in the CSFV-E2 and pan-pestivirus antibody-specific Ceditest ELISAs.

Pestivirus serum antibody-positive but CSPV-negative serum samples (n=96) were randomly obtained from slaughtered adult pigs. Swine sera were tested negative in Ceditest CSFV-E2-specific ELISA (Colijn et al., Vet. Micro. Biol. 59: 15–25, 1997) and positive in the pan-pesti ELISA (Paton et al., J. Virol. Meth. 31: 315–324, 1991; Kramps et al., Vet. Micro. Biol. 64: 135–144, 1999).

CSFV antibody-positive field serum samples tested by virus neutralization test were obtained (n=95) from an infected pig farm (VR) that was infected during the CSF epizootic in the Netherlands in 1997–1998.

Sequential serum samples were collected during a vaccination/challenge experiment of 12 pigs that were vaccinated with E2 and infected with CSFV, strain Brescia. Specific Pathogen-Free (SPF) animals were challenged with the virulent CSFV strain Brescia two weeks after a single vaccination with the E2 subunit vaccine.

Panel of swine sera that were experimentally infected with BVDV (n=5, numbers 4–8).

Panel of swine sera that were experimentally infected with CSFV strain Paderborn (n=5, numbers 9–13).

Panel of bovine sera that were experimentally infected with BVDV (n=9, numbers 1–6, r4590–51, r4590–52, 841).

Reference panel obtained from the European reference laboratory for CSFV: sera from swine that were experimentally infected with CSFV (n=14), BVD (n=1) or BVDV (n=12). Three sera were obtained from swine with experimental mixed infections of BVDV/BDV (n=1) and CSFV/BVDV (n=2).

Pool of hyperimmune sera against CSFV (HIS CSFV).

Pool of hyperimmune sera against BVDV (HIS BVDV).

Solid Phase Peptide ELISA (sp-ELISA)

Test Procedure

For the sp-ELISA, a similar format was chosen as for a previously developed RSV G-peptide ELISA (Langedijk et al., J. Imm. Meth. 193: 153–166, 1996). One microgram of N-terminally acetylated pestivirus peptide was coated per well of a high binding capacity flat bottom microplate (Greiner) in 50 µl of carbonate buffer, pH 9.0, at 37° C. and dried overnight. The optimal dilution of the peptide to coat ELISA plates was chosen in such a manner that maximum binding was obtained as determined in a checkerboard titration. Test sera were titrated. Mouse-anti-swine IgG (23.3.1b) conjugated to horseradish peroxidase (HRP) was diluted 1:1000. Rabbit anti-bovine IgG—HRP (P0159, Dako, Denmark) was diluted 1:1000. Conjugates and test sera were incubated for one hour at 37° C. in ELISA buffer (8.1 mM $Na_2HPO_4$, 2.79 mM $KH_2PO_4$, 0.5 M NaCl, 2.68 mM KCl, 1 mM $Na_2EDTA$, 0.05% v/v Tween 80, pH 7.2) containing 4% horse serum. The substrate chromogen consisted of ABTS/$H_2O_2$. Incubation was performed during 30 minutes at 22° C. OD was measured at 405 nm (Titertek multi scan).

Results

The reactivity of BVDV-positive swine sera (4–8) and CSFV-positive swine sera (9–13) were tested for reactivity in the CSFV sp-ELISA and the BVDV sp-ELISA.

The reactivity of bovine sera (numbers 1–6, r4590–51, r4590–52, 841) were tested for reactivity in the CSFV sp-ELISA and the BVDV sp-ELISA.

Figure 5:
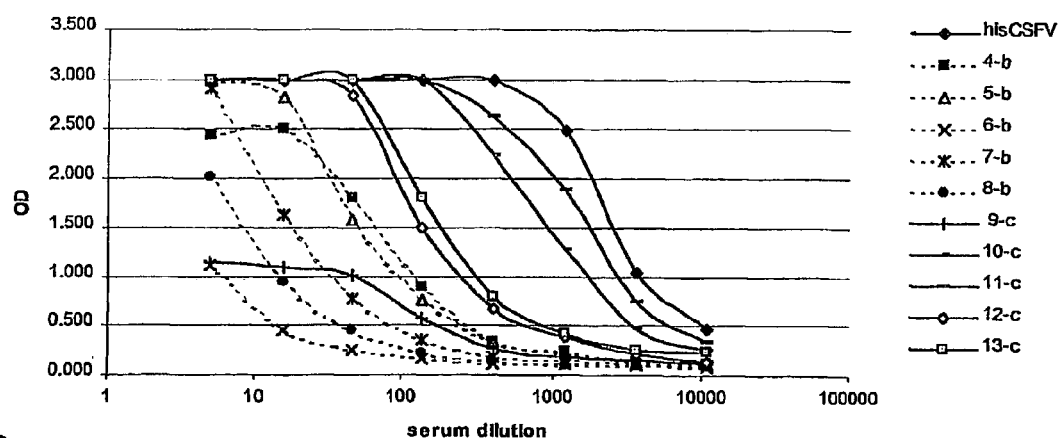
FIGS. 5A and 5B. Reactivity (optical density, OD) in CSFV 1p-peptide ELISA of dilutions of BVDV-specific swine sera (4b–9b) and CSFV-specific swine sera (9c to 13c) and CSFV-specific hyperimmune serum.
FIGS. 5C and 5D Reactivity in CSFV 1p-peptide ELISA of dilutions of BVDV-specific bovine sera (1–6, r4590–51, r4590–52, 841) and BVDV-specific hyperimmune serum.
Figure 5:
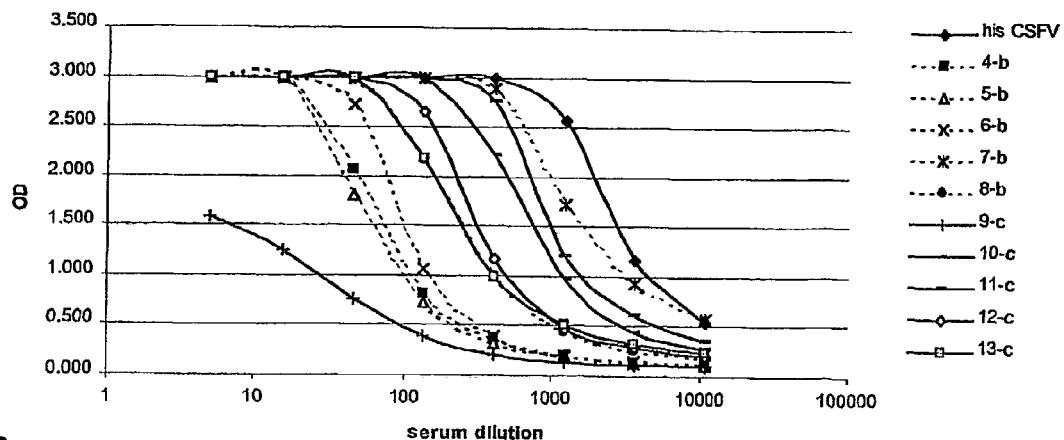
Figure 7:
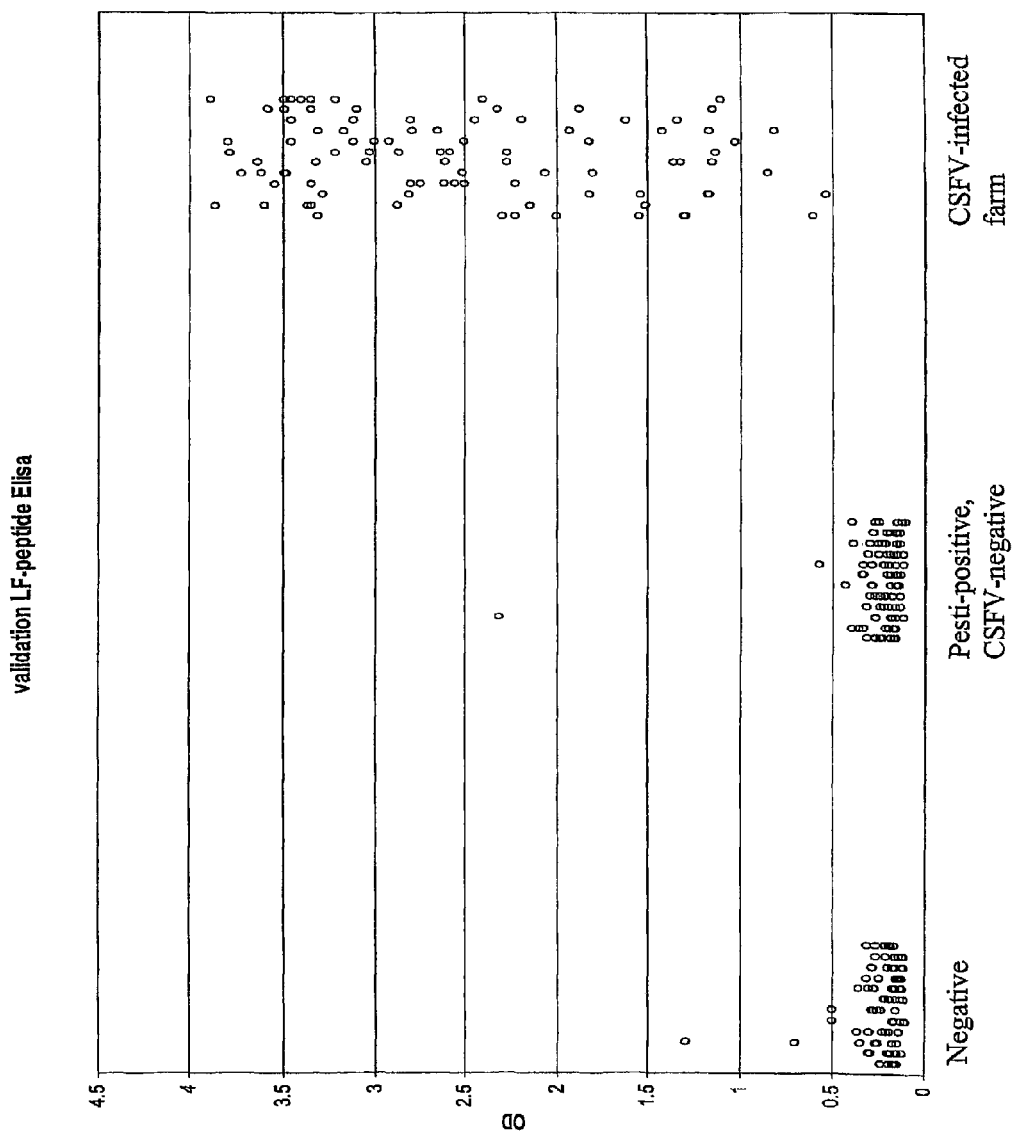
FIG. 7. Reactivity of successive serum samples collected during a vaccination/challenge experiment in the CSFV 1p-peptide ELISA. Twelve pigs were vaccinated with E2, 14 days before challenge.

Reactivity of the sera with the peptides was excellent, which shows that the peptides indeed correspond to an immunodominant region of $E^{ms}$. This agrees with the prediction of the immunodominant character of the subdomain. However, the CSFV and BVDV sera are cross-reactive for both peptides. Although the panel of CSFV-specific swine sera reacted better than the panel of BVDV-specific swine sera in the CSFV ELISA, the reactivities of both panels of sera are similar in the BVDV ELISA. Similarly, the panel of BVDV-specific bovine sera shows high reactivity in the BVDV peptide ELISA (FIG. 5D), but the sera also cross-react considerably in the CSFV ELISA (FIG. 5C).

Liquid Phase Peptide ELISA (1p-ELISA).

Because of the high cross-reactivity in the solid phase peptide ELISA, an ELISA was developed in which the antigen was recognized in liquid phase (1p-ELISA). Moreover, by labeling the homologous peptide of the pestivirus of interest (CSFV peptide), unlabeled heterologous peptide of the cross-reactive pestivirus (BVDV peptide) could be used to block unspecific cross-reactivity.

In the liquid phase peptide ELISA for detection of antibodies against CSFV, the test serum was incubated with a mixture of biotinylated CSFV peptide and acetylated BVDV peptide (without biotin). CSFV-specific antibodies will preferably bind the biotinylated CSFV peptide and BVDV-specific antibodies will preferably bind the nonbiotinylated BVDV peptide. Subsequently, the mixture is transferred to an avidin-coated microtiter plate and the antibodies complexed to the biotinylated CSFV peptide will be caught by avidin and can be detected with an anti-swine peroxidase conjugate and subsequent incubation with substrate.

Test Procedure:

Avidin-coated microtiter plates: 400 ng of ImmunoPure avidine (No. 21121, Pierce, Rockfort, Ill., USA) in 100 µl of carbonate buffer (pH 9) in each well of a high binding capacity flat bottom microplate (Greiner). Plates were covered and incubated overnight at 37° C. After coating, the plates were kept frozen until use.

Before use, the avidin-coated plates were incubated with 100 µl of phosphate-buffered saline (PBS, pH 7) with 10% horse serum per well for two hours at 37° C. on a shaker.

Meanwhile, test serum (1: 50) was incubated with a mixture of 10 ng biotinylated CSFV peptide and 30 ng of BVDV peptide in 100 µl of ELISA buffer with 4% of horse serum for one hour at 37° C.

Avidin-coated plates were washed and 100 µl of test serum and peptide mixture was transferred in the wells and incubated for 45 minutes at 37° C. Subsequently, plates were washed and incubated with 100 µl mouse-anti-swine IgG (23.3.1b) conjugated to horseradish peroxidase (HRP) (Van Zaane et al., 1987) diluted 1:1000 or with rabbit anti-bovine IgG-HRP (P0159, Dako, Denmark) diluted 1:1000. The substrate chromogen consisted of ABTS/$H_2O_2$. Incubation was performed during 30 minutes at 22° C. OD was measured at 405 nm (Titertek, multiscan). Cutoff value was chosenat OD>0.5, which is approximately 3 times the average background of known negative sera.

Results

The reactivity of BVDV-positive swine sera (4–8) and CSFV-positive swine sera (9–13) were tested for reactivity in the CSFV 1p-ELISA (FIGS. 5A–5D). This test format showed much better specificity than the sp-peptide ELISA.

To determine the specificity of the 1p-peptide-ELISA, 96 negative field serum samples were tested in the 1p-peptide-ELISA for CSFV E's-Ab. Only 2 of 96 samples showed a positive response (cutoff was chosen at OD>0.5). Based on these data, the specificity of the 1p-peptide ELISA for CSFV $E^{rns}$-Ab amounts to 98% (=94/96×100%) (FIGS. 6A–6B).

To determine the specificity of the 1p-peptide-ELISA, 96 field sera that contain antibodies directed against other pestiviruses than CSFV (BVDV and BDV) were tested in the 1p-peptide-ELISA. Only 2 of 96 samples showed a positive response (OD>0.5). Based on these data, the specificity of the 1p-peptide ELISA for CSFV $E^{rns}$-Ab for non-CSFV-pestivirus-positive sera amounts to 98% (=94/96×100%) (FIGS. 6A–6B).

To determine the sensitivity of the 1p-peptide-ELISA, 95 field serum samples from a CSFV-infected farm (VR) obtained during the CSF epizootic in the Netherlands in 1997–1998 were tested in the 1p-peptide-ELISA. Not a single serum sample showed a positive response (OD>0.5). Based on these data, the sensitivity of the 1p-peptide ELISA for CSFV antibodies amounts to 100% (FIGS. 6A–6B).

An interesting application of the 1p-peptide ELISA is a diagnostic test that can be used to detect CSFV infection of E2-vaccinated pigs. Therefore, sera of E2-vaccinated pigs should be unreactive in the 1p-peptide ELISA and should be positive after CSFV challenge of the pigs. Successive serum samples, which were collected during a challenge experiment of 12 E2-vaccinated pigs that were infected with CSFV, were tested in the 1p-peptide ELISA (FIG. 7). The results show that all sera but one from E2-vaccinated pigs were negative prior to CSFV challenge. All animals (except one) seroconverted 14 to 28 days after challenge. Finally, the performance of the 1p-peptide ELISA was compared with the E2-based Ceditest ELISA and two other $E^{rns}$-based ELISAs. The reactivity of a panel of European reference sera (see methods) was tested in all four ELISAs (Table 6). Although the E2-based ELISA was superior (one false-negative), the 1p-peptide ELISA performed better (three false-negative) than the other ELISAs based on epitope blocking using complete $E^{rns}$ (5 false-negative, one false-positive, one false-negative and six false-positive). It is very likely that the 1p-peptide ELISA can even be optimized when it is changed into an antibody-blocking format, like the other three ELISAs in Table 6.

To illustrate the compatibility of the peptide ELISA with other pestiviruses, the CSFV-specific peptide ELISA was changed into a BVDV and a BDV ELISA by exchanging the biotinylated CSFV peptide for a biotinylated BVDV peptide or a biotinylated BDV peptide and the acetylated BVD V peptide for the acetylated CSFV. The same amount of peptide was used as in the 1p-CSFV peptide ELISA and all assay conditions were kept similar. The panel of swine sera that were experimentally infected with BVDV (n=5, numbers 4–8) or CSFV (n=5, numbers 9–13) were tested in the three different 1p-peptide ELISAs for the three different pestivirus types. Table 7 shows that BVDV-positive sera react best in the BVDV-specific peptide ELISA and that the CSFV-positive sera react best in the CSFV ELISA, although the CSFV sera cross-react to some extent with the BVDV peptide. As expected, on the basis of the sequence homology, the BVDV and BDV ELISAs show less differentiation. The BVDV and BDV ELISAs both contained acetylated CSFV peptide as competing antigen. Some improvement may be possible when also acetylated BDV and BVDV peptide would be used as competing antigen in the BVDV and BDV ELISAs, respectively.

The acetylated CSFV peptide (Table 2) was further used to test the immunogenicity of the peptide in pigs and to examine whether vaccination with the peptide could protect the pigs after CSFV challenge. Pigs were vaccinated with the various amounts of the peptide, formulated in Freund's Complete Adjuvant (FCA). Four weeks later, the pigs were vaccinated again with 1.3 mg peptide, formulated in Freund's Incomplete Adjuvant (FIA). Five control pigs were vaccinated similarly with just FCA and FIA. Three weeks after the second vaccination, the pigs were challenged nasally with 100 LD50 CSFV, strain Brescia 456610. Antibody reactivity against the peptide was monitored during the experiment. Before and after challenge, virus isolations were performed on white blood cells. After death or euthanasia, organs (tonsil, spleen, kidney and ileum) were tested for the presence of viral antigen using an immunofluorescence test.

Monoclonal Antibody Production

Production of $E^{rns}$ peptide-specific monoclonal antibodies (Mabs) was performed as described (Wensvoort et al., 1986). Two BALB/c mice were immunized intraperitoneally with 400 μg CSFV or BVDV peptide (residues 191–227), mixed with Freund's complete adjuvant (FCA). After four weeks, the mice were boostered with 400 μg of peptide mixed in incomplete FCA, and three weeks later, the mice were boostered with 400 μg of peptide in phosphate-buffered saline. Three days later, the spleen cells were fused with sp20 cells and hybridomas were grown in selective medium. The $E^{rns}$ specificity of the produced Mabs (Mab 906-2-1 (BVDV) and Mab 907-35-1-1 (CSFV)) was determined using an E's antigen detection ELISA. Additionally, the Mabs reacted in the $E^{rns}$ peptide-based ELISAs.

Transport Activity of $E^{rns}$ Peptide.

Test Procedure.

Binding of $E^{rns}$ peptide. Monolayers or cytospins of cell suspensions of several cell types (Ebtr, SK6, sf-21, Caco-2 and HT-29) were fixed with acetone or 4%-paraformaldehyde. Glass slides or coverslips with fixed cells were incubated with biotinylated CSFV peptide (100 or 10 μg/ml PBS) for one hour at 37° C. After washing with PBS, the slips were incubated with avidin-HRP (1: 100, Zymed) or avidin-FITC (1: 70, Zymed) for 30 minutes at 37° C. Cells were inspected for specific binding of the peptide by light microscopy (HRP) or fluorescence microscopy (FITC).

Translocation of $E^{rns}$ peptide. Translocation of the peptide across the plasma membrane was studied by incubation of live cells in suspension or subconfluent monolayers on coverslips with biotinylated peptide (200 to 0.4 μg/ml culture medium) for 1, 10, 30, 45 or 180 minutes. After the time period, cells were fixed with 4% paraformaldehyde or cold methanol and labeled with avidin-FITC as described above. Fixed cells were inspected with fluorescence microscopy. Internalization was established with confocal microscopy. The following cell lines were used: A72, canine fibroblast tumor cells; MDCK, canine kidney epithelial cells; CCO, sheat-fish ovaria cells; EK-1, eel kidney cells; CHS-E, salmon embryonal cells; BUEC, bovine umbilical endothelial cells; BFDL, bovine fetal diploid lung cells (fibroblast); PUEC, porcine umbilical endothelial cells; HT 29, colorectal adenocarcinoma, colon epithelial cells; CaCo-2, colorectal adenocarcinoma, colon epithelial cells; Hela, adenocarcinoma, cervix; Vero, normal monkey kidney epithelial cells; SK6, swine kidney cells; NPTh, newborn pig thyroid cells; ECTC, embryonal calf thyroid cells; MDBK, normal bovine kidney epithelial cells; EBTr, epithelial bovine trachea cells; Bovine sperm cells; Sp20 mouse myeloma B-cells.

Transepithelial transport. The potential of $E^{ms}$ peptide to permeabilize epithelium and assist transport of molecules across epithelium was tested in USSING chambers of the snapwell type with CaCo-2 or HT29 cells that closely mimic epithelial cell sheets.

The potential of $E^{ms}$ peptide to carry nonlinked molecules across epithelium was tested by mixing HRP (0.08 µg/ml culture medium) with several concentrations of $E^{ms}$ peptide (50, 5 and 0.5 µg/ml ringers medium) in the upper chamber. Samples were drawn from the lower chamber after 15, 30, 45, 60, 120 and 240 minutes, which were tested for HRP concentration.

Transdermal transport. The potential of the an $E^{ms}$ peptide to penetrate the skin was tested by applying 150 µl 0.3–4 mM of biotinylated peptide in a chamber containing an isolated piece of "fresh" human breast skin or in a chamber which was glued on the skin of a live pig, or applying 50 µl of peptide solution on the skin with a cotton wool tip, or applying 50 µl of a peptide solution mixed with 50 µl of contact gel on the skin for 30 minutes to 120 minutes. After the incubation time, the pig was killed, the skin was cleaned and biopsied, and a biopsy was frozen in liquid nitrogen. Cryosections of the skin samples were fixed on microscopic slides with acetone and incubated with streptavidin-FITC (1/100) for 30 minutes.

Hemolytic assay. Hemolytic activity of various peptide concentrations was determined by incubation with human, guinea pig or sheep erythrocyte suspensions (final erythrocyte concentration, 1% v/v) for one hour at 37° C. After cooling and centrifugation, the optical density of the supernatants was measured at 540 nm. Peptide concentrations causing 50% hemolysis ($EC_{50}$) were derived from the dose-response curves.

Clonogenicity of mammalian cells. HeLa or EBTr cells were cultured in DMEM, supplemented with 20% fetal bovine serum and antibiotics in a humidified atmosphere supplied with 5% $CO_2$ at 37° C. Exponentially growing cells were treated with trypsin and transferred to wells of a 96-well microtiter plate, resulting in approximately 300 cells for each 30 µl of growth medium containing various concentrations of peptide. After incubation for 75 minutes (the plates were incubated upside down to avoid anchorage), the cells were transferred and plated in wells of tissue culture plates, which contained 100 µl of growth medium. Cell growth was checked after 3 to 6 days.

Antimicrobial assay. Two bacterial strains (*Escherichia coli* ATCC 25922 and *Enterococcus faecalis* ATCC 29212) were inoculated on heart infusion agar with 5% sheep blood and incubated aerobically overnight at 37° C. From the pure cultures, suspensions were made in saline to a density of 0.5 McFarland. These suspensions were diluted ten-fold in Mueller Hinton II broth, resulting in a final inoculum of approximately $10^7$ cfu/ml.

Standard 96-well microtiter trays were filled with 100 µl of two-fold dilutions of peptide in physiologic salt solution in each well, resulting in the following concentration range: 4000, 2000, 1000, 500, 250, 125, 62.25, 31.63, 15.82, 7.96 and 0 µg/ml. The trays in column 12 were filled with 200 µl MH II broth (negative control).

Columns 1–11 of the microtiter trays were filled with 100 µl of the final inoculum of the bacterial suspensions, thus diluting the concentrations of the peptide two fold, resulting in the following peptide concentration range in the wells: 2000, 1000, 500, 250, 125, 62.25, 31.63, 15.82, 7.96, 3.98 and 0 µg/ml. In rows B, C and D, 100 µl of the final inoculum of *E. coli* and, in rows E, F and G, 100 µl of the final inoculum of *E. faecalis* was pipetted. The final bacterial concentration was approximately $5 \times 10^5$ cfu/well. All trays were sealed and incubated overnight at 37° C. After incubation, the microtiter trays were inspected visually for bacterial growth and the absorbance of the cultures at 630 nm ($A_{630}$) was determined with an ELISA-reader. The peptide concentrations in the wells with the lowest concentrations that showed no visible growth or increase in absorbance compared with the negative control wells were considered to be the Minimum Inhibitory Concentrations (MICs). The experiment was performed independently in triplicate. The test was repeated again in triplicate after two days with the final peptide concentration range in the wells: 5000, 2500, 1250, 625, 312.5, 156.25, 78.12, 39.06, 19.58, 9.79, 4.88, 2.44 and 1.22 µg/ml.

Peptide synthesis. A panel of truncated $E^{ms}$ peptides was synthesized to elucidate the minimal membrane-active region. A panel of truncated restrictocin L3 peptides was synthesized to elucidate the minimal membrane-active region. Substitutions in the amino acid sequence of the transport peptide module can be applied to increase the translocation activity. An optimized transport peptide can, for example, be synthesized according to retro-inverso peptide chemistry, in which the sequence is reversed and D-amino acids are used instead of L-amino acids. Synthesis is performed as described above.

Coupling of peptide to oligonucleotide. The optimized $E^{ms}$ peptide contains a Broom-acetic acid at its N-terminus (Broom-GRQLRIAGKRLEGRSK) (SEQ ID NO:25) coupled to two sulfhydryl groups at the 5'- and the 3'-end of an FITC-labeled 32 residue long oligonucleotide (Thiol-$GT^{FITC}$CCCACCGAGGCTAGCTACAAC-GACCCTTATAT-thiol) (SEQ ID NO:26).

Results

To determine the binding of the $E^{ms}$ peptide, biotinylated CSFV peptide was incubated with various fixed cells. Binding was determined after incubation with avidin-HRP or avidin-FITC. Biotinylated CSFV peptide was able to bind to all tested cell types. There was a marked difference between the binding to paraformaldehyde versus acetone-fixed cells. In contrast to the paraformaldehyde-fixed cells, the acetone-fixed cells showed less binding with the peptide. Because much of the membrane fraction gets washed away after acetone-fixation, this suggests that the peptide may bind to the membrane.

Figure 8:
FIGS. 8A–8C. Distribution of biotinylated CSFV E$^{ms}$ peptide (8A, 8C) and biotinylated control peptide (8B) (25 µM) after 30 minutes of incubation with subconfluent EBTr cells grown on a 10-well microscope slide. Cells were fixed with cold methanol and biotinylated peptide was visualized by staining with avidin-FITC for 30 minutes. Fluorescent micrograph (250×) (8A, 8B) or fluorescent micrograph using confocal microscope (600×) (8C).
Figure 8:
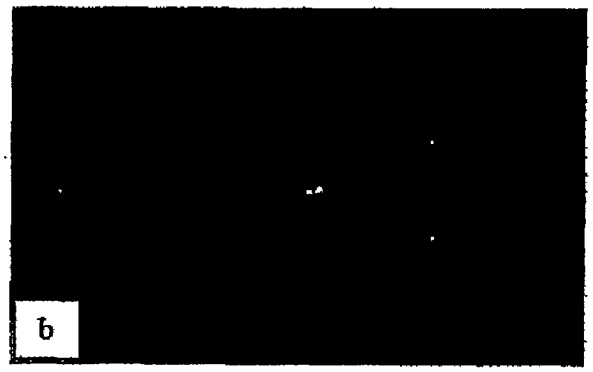
Figure 8:
Figure 9:
FIGS. 9A and 9B. Distribution of biotinylated L3 peptide (9A) and magainin-1 peptide (9B) (6 µM) after 30 minutes of incubation with subconfluent EBTr cells grown on a 10-well microscope slide. Cells were fixed with cold methanol and biotinylated peptide was visualized by staining with avidin-FITC for 30 minutes. Fluorescent micrograph (250×).
Figure 9:
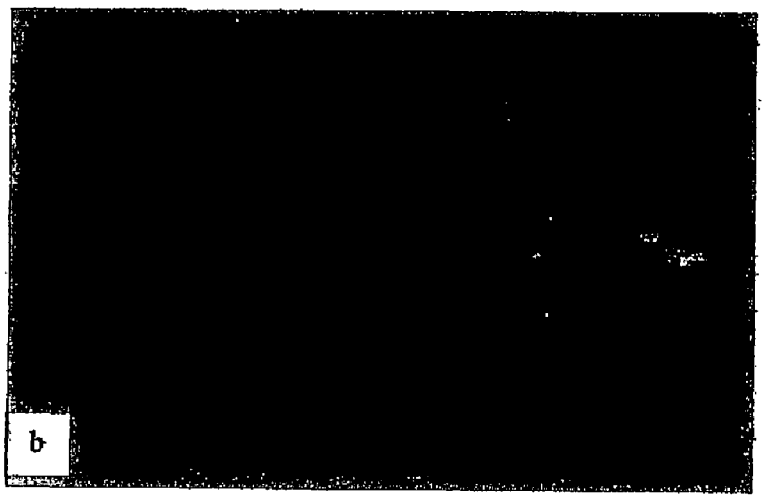
Figure 10:
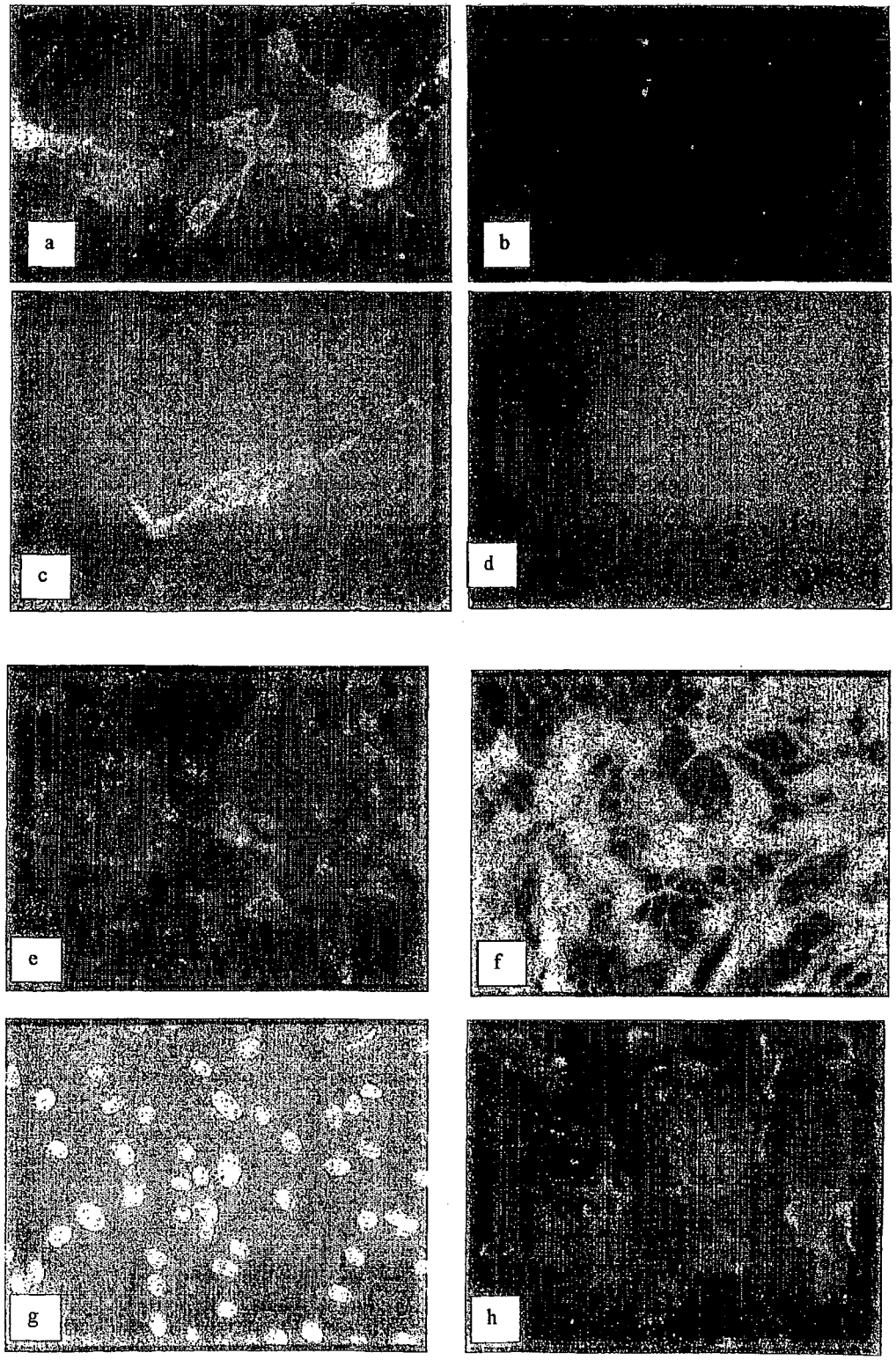
FIGS. 10A–10H. Transport of avidin and streptavidin. Equimolar amounts of avidin-Texas Red (66 kD) (10A) or streptavidin-FITC (60 kD) (10C) were mixed with the biotinylated E$^{ms}$ peptide or unbiotinylated peptide (10B, 10D) (residues 194–220) (3 µM) and incubated with EBTr cells for 30 minutes. Transport of a complex of streptavidin-FITC with optimized E$^{ms}$ peptide biotin-GRQLRIAGRRLR-GRSR (SEQ ID NO:39) (10E), optimized E$^{ms}$ peptide biotin-GRQLRRAGRRLRRRSR (SEQ ID NO:40) (10F), HRSV-G type A peptide biotin-KRPNKKPGKKTTTPT-KKPTIKTTKKDLKPQTTKPK (SEQ ID NO:41) (10G) and HRSV-G type A biotin-KRIPNKKPGKKT (SEQ ID NO:42) (10H).
Figure 11A:
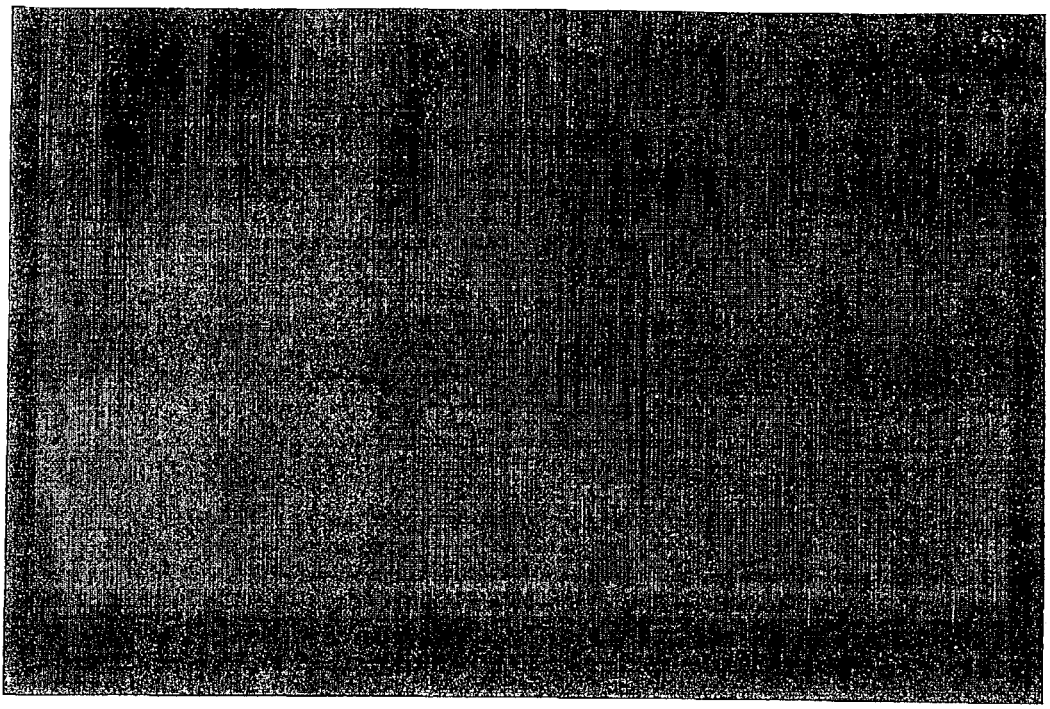
FIGS. 11A and 11B. Distribution of FITC-labeled oligonucleotide (32 nt) (11A) and FITC-labeled oligo coupled to optimized E$^{ms}$ peptide (11B) at 56 µg oligo/ml after 30 minutes incubation with cells.
Figure 11B:
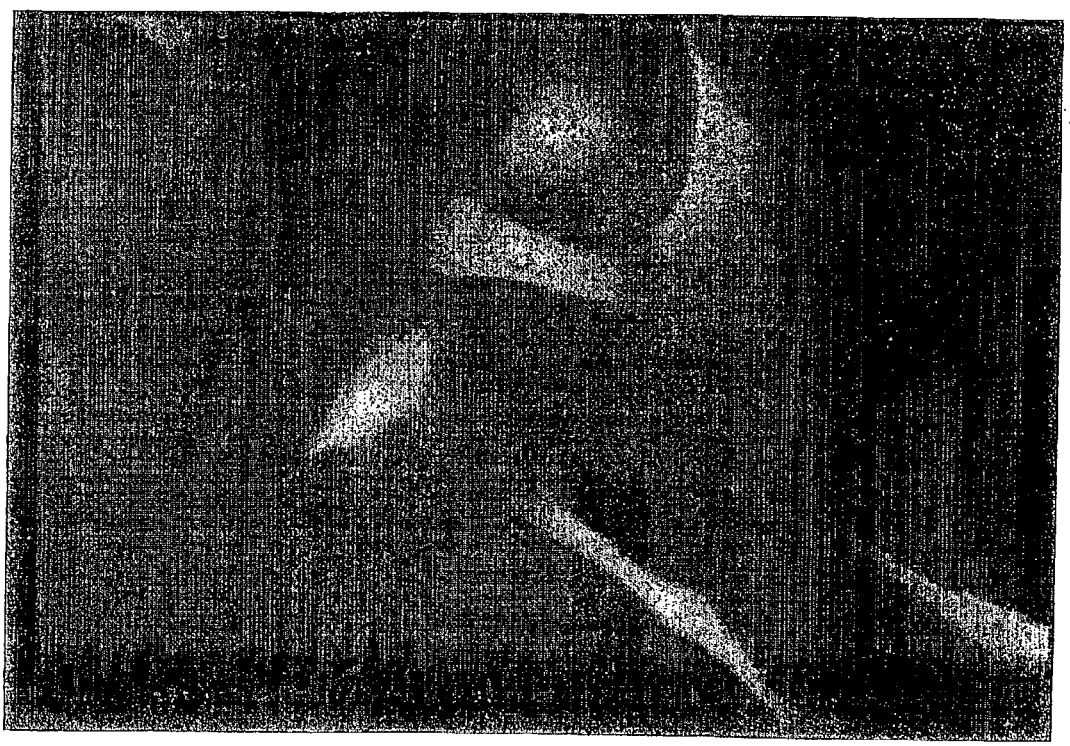
Figure 12:
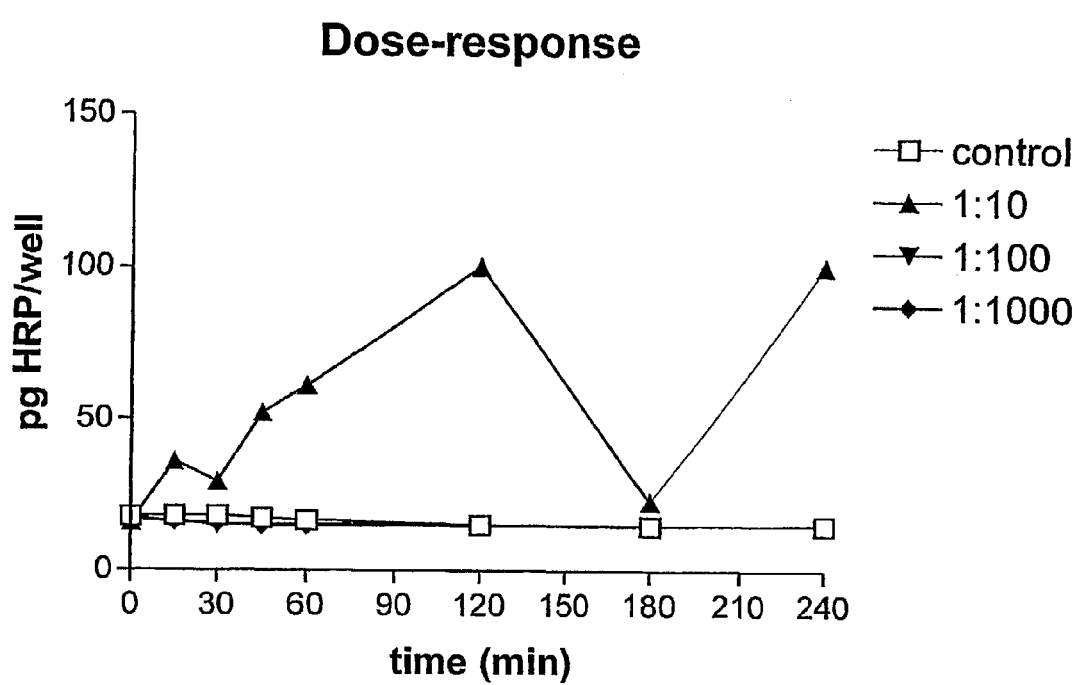
FIG. 12. Passage of HRP through epithelial cell sheet incubated with 0, 0.5, 5 and 50 µg/ml BVDV E$^{ms}$ peptide.

Next, cell suspensions (mouse myeloma and bovine sperm) and subconfluent monolayers of various cell types (see test procedure) were incubated with biotinylated CSFV peptide and fixed after different time intervals. Inspection with fluorescent microscopy and confocal microscopy showed that the peptide had penetrated inside all cell types. The peptide entered the cell within one minute, and optimal fluorescence was established after 30 minutes (FIG. 8). Peptide was translocated to specific regions inside the nucleus, which may be the nucleoli. Peptide was also distributed around the nucleus in membranous parts in the cytosol. The colocalization in the nucleoli was established by double staining with acridinorange (Merck, Darmstadt, Germany) and streptavidin—Texas red. Yellow fluorescence was observed which indicates colocalization of peptide and nucleoli stain. Next, the membrane-active region of the peptide was precisely defined by testing the translocation activity of a panel of truncations of the $E^{ms}$ peptide and some peptides with N-terminal additions and C-terminal deletions (Table 8). Translocation to the nucleus was more effective with the CSFV, strain Alfort, $E^{ms}$ peptide compared to the BVDV or BDV $E^{ms}$ peptide. The CSFV, strain Alfort, $E^{ms}$ peptide translocated also more effectively than the CSFV peptide corresponding to strains in which positions 209, 210 and 217 were substituted. Furthermore, deletion of the seven most C-terminal residues and the three N-terminal residues increased the nuclear translocation activity of the peptide. To reduce the length of the transport peptide further, the region responsible for translocation (residues 194–220) was truncated while arginines were introduced to maintain or enhance the translocation activity. N-terminal deletions were made of 4 and 5 residues and one extra arginine was introduced at the same face of the presumed helix. These shorter peptides retained translocation activity (Table 9). Next, 11 N-terminal residues were deleted and the glutamic acid was substituted by arginine. This substitution enhanced the translocation activity by a factor of 33. Replacing the two lysine residues by arginine residues enhanced the translocation activity by an additional factor of three. Introducing more arginines in the sequence did not improve the translocation activity of the biotinylated peptide (Table 9). Next, the optimized peptide (MDK-20) was synthesized with D-amino acids according to the retro-inverso approach with an additional lysine-MTT (peptide A941: biotin-rsrgrlrrgairlqrgK (SEQ ID NO:27 (MTT)-BrHAc). This peptide retained its translocation activity and showed even a higher translocation activity compared with the original MDK-20, showing the advantages of the retro-inverso approach.

Because of the homology between the $E^{ms}$ peptide, magainin and the L3 loop peptide, the biotinylated magainin and L3 loop peptide were also tested for translocation activity. L3 showed translocation activity, magainin did not (FIG. 9). Next, the membrane-active region of the peptide responsible for translocation was precisely defined by testing the translocation activity of a panel of truncations of the L3 peptide (Table 10). To elucidate general rules for peptide translocation, we searched for new transport peptides and tested them for translocation across the plasma membrane.

HIV-1 tat peptide, which is a transcription factor that binds. DNA, the AntP peptide, which is a homeobox protein, and transportan, which is a hybrid peptide of a bee venom, and galparan. The only similarity between the known transport peptides is the content of basic residues. See also Wender, P. A. et al., 2000, Proc. Natl. Acad. Sci. USA, 97: 13003–8, who, however, require high >50% arginine content.

To search for more transport peptides, we tested the translocation of basic peptides which were derived from linear DNA-binding motifs; RNA-binding motifs; heparin-binding motifs, basic enzymatic cleavage sites and nuclear localization signals. For nuclear localization signals (NLS), it is already known that they are able to translocate the nuclear membrane, although it is thought that they need to be recognized by a receptor in order to translocate. We tested whether peptides corresponding to nuclear localization sites could also be used as general transport peptides that cross the plasma membrane.

Several types of short transport peptides were found:

Monopartite: PKKKRKV (SEQ ID NO:28). Binds the import receptor

Imp Alpha/Imp Beta Complex.

This sequence is identical to the NLS of simian virus 40 large T antigen.

Bipartite: KRPAAIKKAGQAKKKK (SEQ ID NO:29) (lysine-rich signals).

NLS of HIV-1 Rev RQARRNRRRRWR (SEQ ID NO:30).

HIV-1 rev is a viral RNA export factor and shuttles RNA outside the nucleus. The sequence motif binds RNA.

A synthetic peptide has been developed (RSG-1.2) that binds the Rev binding site RNA with 10 times higher affinity

DRRRRGSRPSGAERRRRR (SEQ ID NO: 31)

NLS of human herpesvirus-8 K8 protein TRRSKRRSHRKF (SEQ ID NO:32).

K8 protein is homologous to EB1 protein of Epstein-Barr virus (EBV), which is a transcriptional activator which directly binds specific sites on the DNA.

Another class of basic peptides that may in some cases also be NLS peptides are RNA/DNA-binding peptides. For instance, the HIV-1 Rev peptide also binds directly to RNA.

Other examples of peptides that bind DNA or RNA:

RNA-binding element of flockhouse virus (FHV) NRTRRNRRRVR (SEQ ID NO:33).

RNA-binding element of bacteriophage lambda-N QTRRRERRAEKQAQW (SEQ ID NO:34).

Another class of basic peptides are basic enzymatic cleavage sites.

An example of a viral enzymatic cleavage site is in the surface proteins of alpha viruses. The cleavage site between E3 and E2 is highly basic. After cleavage, it is the C-terminal region of E3 which is located at the distal end of the viral spike, interacting primarily with E2.

Western equine encephalitis virus E3: KCPSRRPKR (SEQ ID NO:35).

Other examples of basic peptides are linear heparin-binding sites. The transport peptide corresponding to the $E^{ms}$ C-terminal domain also binds heparin. Examples are peptides found in HRSV-G, type A: KRIPNKKPGKKTTTKPTKKPTIKTTKKDLKPQTTKPK (SEQ ID NO:36) and HRSV-G, type B: KSICKTIPSNKPKKK (SEQ ID NO:37).

These peptides showed translocation activity (Table 11). In the case of the heparin-binding sites of HRSV-G, the region responsible for translocation was mapped (Table 11). One of the most active HRSV-G peptides (Biotin-KRIPNKKPKK) (SEQ ID NO:38) was further optimized by changing all lysine residues into arginine residues to check whether the peptide showed higher translocation activity when residues were introduced which were more basic. Changing the four lysines to arginines improved the translocation activity by a factor of three (Table 11).

According to Table 9, the most active biotinylated peptide (residues 194–220) was still (faintly) detectable at 125 nM. As a result, the elucidation of the minimal essential part of the translocation peptide also proves that a C-terminal cargo of at least 6 residues can be transported and an N-terminal cargo of at least 13 residues plus a biotin can be transported. Because the peptide is probably also able to transport the RNase domain of $E^{ms}$ inside the cell, it is also expected that large proteins can be transported by the peptide. After mixing equimolar amounts of streptavidin-FITC (60 kD, nonglycosylated, neutral) with the most active $E^{ms}$ peptide (residues 194–220) and with an optimized $E^{ms}$ peptide (biotin-GRQLRIAGKRLEGRSK) (SEQ ID NO:25), it was possible to transport streptavidin-FITC inside the cell and the nucleus (FIG. 10). The peptides were also able to carry avidin-Texas Red (66 kD, glycosylated, positively charged) inside the cells. Also, the optimized $E^{ms}$ peptides and the long and short HRSV-G type A peptides (MDN-12 and MDP-32 according to Table 11) were tested for their ability to transport streptavidin-FITC into the cell (FIGS. 10F–10H). The translocation activity of the peptide complexed to the streptavidin cargo was different from the translocation of the biotinylated peptide alone. The optimized $E^{ms}$ peptide MDM-27, which has two additional positive charges compared to the optimized E$^{rns}$ peptide MDK-20, transports streptavidin-FITC much better than MDK-20. In contrast, in the case of the uncomplexed biotinylated peptide, the translocation activity was similar. This effect was even more pronounced when the longer HRSV-G peptide (MDN-12) was compared to the shorter HRSV-G peptide (MDP-32), which has less positive charge but higher translocation activity as a single, uncomplexed molecule without cargo (FIGS. 10G and 10H).

To check whether the transport peptide was also able to transport proteins that retain biological activity, the peptide was complexed with streptavidin conjugated to the enzyme β-galactosidase (600 kD). The complex was transported efficiently into the cells and retained its ability to release nonreducing terminal galactose. To check whether the peptides could transport oligonucleotides, the optimized E$^{rns}$ peptide was activated by a Broomacetic acid. Transport module Broom-GRQLRIAGRRLRGRSR (SEQ ID NO:39) was coupled to an FITC-labeled 32 oligonucleotide at the 5'- and the 3'-end. The complex was tested for translocation inside the cell and the nucleus. Titration of the uncoupled oligonucleotide and the complex of peptide and oligo showed that the intracellular accumulation of the oligonucleotide was 75 times higher when it was coupled to the transport peptide. To check whether the membrane destabilizing activity had a general toxic effect on cells, leakage of the cell was tested for tryphan blue after peptide incubation of 30 minutes. Only at high concentrations of peptide (>35 µM), some tryphan blue could be determined inside the cell, especially in isolated areas in the nucleus.

Hemolysis of erythrocytes can also be indicative for lytic effect of the peptides on eukaryotic cell membranes. Hemolysis of erythrocytes from several species was tested with the panel of E$^{rns}$ peptides (Table 8). The different peptides show a broad range of hemolytic activities on guinea pig erythrocytes. The peptide with the highest translocation activity (residues 194–220) has a low hemolytic activity. No significant hemolysis was observed with sheep and human erythrocytes. The effect of the E$^{rns}$ peptide on cell growth of HeLa cells and EBTr cells was determined in a clonogenicity assay as shown in Table 12. These data correspond to the other toxicity assays and indicate that the translocation activity is much higher than the cytotoxic activity.

Transdermal Transport.

Next, it was tested whether the optimized E$^{rns}$ peptide (MDK-20) was able to penetrate an epithelial layer. Because of the stratum corneum layer, the skin seems to be the most difficult epithelial barrier to take. To test the penetration by the biotinylated peptide, a sample of human breast skin was contacted with the biotinylated peptide in vitro during two hours. In fixed cryosections of the skin, the biotinylated peptide could be visualized with streptavidin-FITC in the epidermis and the dermis (FIG. 13). The same results were obtained when the peptide was contacted with the skin of a pig in vivo. As soon as 30 minutes after application, penetration of the peptide into the epidermis was observed. Because of the high amount of proteolytic enzymes in the skin, transdermal transport was also tested with the stable retro-inverso peptide containing D-amino acids. Much more accumulation in the skin was observed for the peptide with D-amino acids (A941) compared with the original peptide containing L-amino acids (MDK-20)

Trans epithelial transport. Next, the peptide was tested for the ability to assist leakage of proteins through an epithelial cell sheet. Horseradish Peroxidase, which was mixed with the peptide, could be transferred through the cell sheet.

Antibacterial activity. Because of the membrane activity and the homology with antibacterial peptides, the antibacterial activities of the peptides were determined as described above. The peptides indeed showed antibacterial activity against the gram-negative E. coli (Table 13) but not against E. faecalis. The MICs against E. coli correlate with the translocation activity of the peptide. The restrictocin L3 peptide showed no antibacterial activity.

TABLE 5

| | |
|---|---|
| Restrictocin | (SEQ ID NO:5)<br>GNGKLIKGRTPIKFGKADCDRPPKHSQNGMGK |
| Mitogillin | (SEQ ID NO:5)<br>-------------------------------- |
| Toxin AspfI | (SEQ ID NO:5)<br>-------------------------------- |
| Alpha-sarcin | (SEQ ID NO:6)<br>-D---P----------S---------KD-N-- |
| Gigantin | (SEQ ID NO:7)<br>-E--IL----------S---------KD-N-- |
| Clavin | (SEQ ID NO:8)<br>-D--IL-------W-NS---------K--D-- |

TABLE 6

Comparison of reactivity of reference sera with different CSFV diagnostic tests

| No | DPI[1] | Inoculum | E2-ELISA Cedi-E2[2] | E$^{RNS}$ ELISA Cedi-Erns[3] | E$^{RNS}$ ELISA Bom-melie[4] | Peptide |
|---|---|---|---|---|---|---|
| 1 | 43 | CSFV Visbek/Han 95 | + | + | + | 0.171 |
| 2 | 16 | CSFV Visbek/Han 95 | + | + | + | 0.477 |
| 3 | 20 | CSFV Visbek/Han 95 | + | + | + | 1.796 |
| 4 | 20 | CSFV Visbek/Han 95 | + | − | + | 3.165 |
| 5 | 14 | CSFV Visbek/Han 95 | + | + | + | 0.7 |
| 6 | 21 | CSFV Alfort 187 | + | − | − | 0.186 |
| 7 | 29 | CSFV Diepholz1/Han 94 | + | + | + | 2.25 |
| 8 | 29 | CSFV Diepholz1/Han 94 | + | − | + | 2.619 |
| 9 | 29 | CSFV Diepholz1/Han 94 | + | − | + | 1.857 |
| 10 | 34 | CSFV Visbek/Han95 | + | − | + | 3.87 |
| 11 | 55 | CSFV Visbek/Han95 | + | + | + | 1.122 |
| 12 | 93 | CSFV C-strain | + | + | + | 0.543 |
| 13 | 69 | CSFV Diepholz1/Han 94 | + | + | + | 2.146 |
| 14 | 28 | CSFV Diepholzl/Han 94 | − | + | + | 1.103 |
| 15 | | BVDV NADL | − | − | − | 0.103 |
| 16 | | BDV | − | − | − | 0.45 |
| 17 | | BVDV 2214 | − | + | + | 0.161 |

TABLE 6-continued

Comparison of reactivity of reference sera with different CSFV diagnostic tests

| | | | E2-ELISA | $E^{RNS}$ ELISA | | |
|---|---|---|---|---|---|---|
| No | DPI[1] | Inoculum | Cedi-E2[2] | Cedi-Erns[3] | Bommelie[4] | Peptide |
| 18 | | BVDV NADL | − | − | − | 0.118 |
| 19 | | BVDV NADL + BDV | − | − | + | 0.136 |
| 20 | | BVDV + CSFV Alfort 187 | + | + | + | 3.208 |
| 21 | | BVDV Osloss | − | − | − | 0.146 |
| 22 | | BVDV Osloss | − | − | − | 0.151 |
| 23 | | BVDV Osloss | − | − | − | 0.151 |
| 24 | | BVDV Osloss | − | − | − | 0.162 |
| 25 | | BVDV Osloss | − | − | − | 0.172 |
| 26 | | BVDV Osloss | − | − | + | 0.164 |
| 27 | | BVDV Osloss | − | − | + | 0.149 |
| 28 | | BVDV Osloss | − | − | + | 0.163 |
| 29 | | BVDV Osloss | − | − | + | 0.215 |
| 30 | | CSFV Alfort 187 + BVDV Osloss | + | + | + | 0.567 |

[1]Days post infection. Serum numbers 21–29 obtained from same animal
[2]Cedi-E2 assay registration no.: BFAV/KSP/D10/98
[3]Cedi-Erns assay
[4]Bommeli AG/Intervet assay

TABLE 7

Comparison of reactivity (OD 405) in different Pestivirus peptide ELISAs

| Serum number | CSFV | BVDV | BDV |
|---|---|---|---|
| 4 BVDV | 0.236 | 1.346 | 0.781 |
| 5 BVDV | 0.129 | 0.724 | 0.388 |
| 6 BVDV | 0.106 | 3.211 | 0.824 |
| 7 BVDV | 0.250 | 4.000 | 4.000 |
| 8 BVDV | 0.104 | 4.000 | 2.325 |
| 9 CSFV | 0.487 | 0.367 | 0.349 |
| 10 CSFV | 2.090 | 1.612 | 0.343 |
| 11 CSFV | 2.555 | 0.610 | 0.246 |
| 12 CSFV | 1.133 | 0.453 | 0.412 |
| 13 CSFV | 1.253 | 0.573 | 0.436 |
| HIS CSFV 1:500 | 2.263 | 0.471 | 0.624 |
| HIS CSFV 1:1000 | 1.419 | 0.267 | 0.356 |
| HIS CSFV 1:2000 | 0.871 | 0.166 | 0.180 |
| Negative serum | 0.152 | 0.150 | 0.153 |

All sera were diluted 1:50 except for the HIS sera

TABLE 8

Determination of minimal membrane-active sequence of $E^{ms}$.

| Residue number | Sequence[1] | | Cellular fluorescence | Nuclear fluorescence | Hemolysis (mg/ml) |
|---|---|---|---|---|---|
| 191–227 | $ENARQGAARVTSWLGRQLRIAGKRLEGRSKTWFGAYA#-COOH | (SEQ ID NO:16) | ++++ | ++ | 0.07 |
| 191–227[2] | $ENARQGAARVTSWLGRQL*STAGKRLE\**RSKTWFGAYA#-COOH | (SEQ ID NO:43) | +++ | + | 0.08 |
| 191–227 | $ENARQGAAKLTSWLGKQLGIMGKKLEHHSKTWFGANA-COOH | (SEQ ID NO:44) | ++++ | + | 0.25 |
| 194–230[3] | $EGARQG*TAKLTT*WLGKQLGTAGKKLE*NK*SKTWFGAYA# | (SEQ ID NO:45) | ++++ | + | 0.25 |
| 184–223 | $DGMTNTIENARQGAARVTSWLGRQLRIAGKRLEGRSKTWF# | (SEQ ID NO:46) | ++++ | ++ | 0.15 |
| 181–220 | $YLLDGMTNTIENARQGAARVTSWLGRQLRIAGKRLEGRSK# | (SEQ ID NO:47) | ++++ | +++ | 0.09 |
| 177–216 | $DTALYLLDGMTNTIENARQGAARVTSWLGRQLRIAGKRLE# | (SEQ ID NO:48) | ++ | − | 0.23 |
| 172–211 | $GSLLQDTALYLLDGMTNTIENARQGAARVTSWLGRQLRIA# | (SEQ ID NO:49) | + | − | >0.33 |
| 191–223 | $ENARQGAARVTSWLGRQLRIAGKRLEGRSKTWF# | (SEQ ID NO:50) | +++ | +++ | 0.15 |
| 191–220 | $ENARQGAARVTSWLGRQLRIAGKRLEGRSK# | (SEQ ID NO:51) | +++ | +++ | 0.31 |
| 191–216 | $ENARQGAARVTSWLGRQLRIAGKRLE# | (SEQ ID NO:52) | ++ | + | >0.33 |
| 191–211 | $ENARQGAARVTSWLGRQLRIA# | (SEQ ID NO:53) | + | − | >0.33 |
| 194–220[4] | $RQGAARVTSWLGRQLRIAGKRLEGRSK# | (SEQ ID NO:1) | ++++ | ++++ | 0.26 |
| 196–220 | $GAARVTSWLGRQLRIAGKRLEGRSK# | (SEQ ID NO:54) | +++ | ++ | 0.16 |
| 199–220 | $RVTSWLGRQLRIAGKRLEGRSK# | (SEQ ID NO:55) | ++ | + | 0.18 |

TABLE 8-continued

Determination of minimal membrane-active sequence of $E^{ms}$.

| Residue number | Sequence[1] | | Cellular fluorescence | Nuclear fluorescence | Hemolysis (mg/ml) |
|---|---|---|---|---|---|
| 202–220 | $SWLGRQLRIAGKRLEGRSK# | (SEQ ID NO:56) | + | + | >0.33 |
| 205–220 | $GRQLRIAGKRLEGRSK# | (SEQ ID NO:25) | + | – | >0.33 |
| MAGAININ | $GIGKFLHSAGKFGKAFVGEIMKS# | (SEQ ID NO:24) | – | – | ? |
| L3 loop 59–88 | $GNGKLIKGRTPIKFGKADCDRPPKHSQNGMGK# | (SEQ ID NO:5) | ++++ | ++++ | ? |

[1] $ = biotin, # = amide, * = mixture of G and R at that position of the peptide, bold italic residues differ from $E^{ms}$ of CSFV, strain Alfort.
[2] sequence corresponds to distinct CSFV strains present in sequence database.
[3] sequence corresponds BVDV, strain M96751.
[4] sequence of peptide which showed highest activity.

TABLE 9

Optimization of Erns peptide

| peptide | Code | Sequence | | Concentration (μM) |
|---|---|---|---|---|
| Translocation domain $E^{ms}$ according to Table 8 | MDB-17 | Biotin-RQGAARVTSWLGRQLRIAGKRLEGRSK-NH2 | (SEQ ID NO:1) | 1.0 |
| | MDL-8 | Biotin-RRVTSWLGRQLRIAGKRLEGRSK-NH2 | (SEQ ID NO:57) | 1.0 |
| | MDL-9 | Biotin-RVRSWLGRQLRIAGKRLEGRSK-NH2 | (SEQ ID NO:58) | 1.0 |
| | MDA-19 | Biotin-GRQLRIAGKRLEGRSK-NH2 | (SEQ ID NO:25) | 10 |
| | MDR-25 | Biotin-GRQLRIAGKRLRGRSK-NH2 | (SEQ ID NO:59) | 0.3 |
| Optimized transport peptide (movin) | MDK-20 | Biotin-GRQLRIAGRRLRGRSR-NH2 | (SEQ ID NO:39) | 0.1 |
| Rhodamine labeled | A931 | Rhodamine-GRQLRIAGRRLRGRSR-NH2 | (SEQ ID NO:39) | 3.0 |
| Mutations in movin | MDM-25 | Biotin-GRQLRRAGRRLRGRSR-NH2 | (SEQ ID NO:60) | 0.1 |
| | MDM-26 | Biotin-GRQLRIAGRRLRRRSR-NH2 | (SEQ ID NO:61) | 0.1 |
| | MDM-27 | Biotin-GRQLRRAGRRLRRRSR-NH2 | (SEQ ID NO:40) | 0.1 |
| Shorter version of movin | MDM-28 | Biotin-RQLRIAGRRLRGRSR-NH2 | (SEQ ID NO:62) | 0.1 |
| Movin + bromoacetic acid biotine with D-aminozuren (retro-inverso) | A941 | Biotine-RSRGRLRRGAIRLQRG-Lysine(MTT)-broomacetic acid | (SEQ ID NO:63) | 0.03 |

TABLE 10

Mapping of restrictocin L3 loop

| Peptide | Sequence | | Concentration (μM) |
|---|---|---|---|
| Restrictocin L3 | Biotin-GNGKLIKGRTPIKFGKADCDRPPKHSQNGMGK-NH2 | | 1.0 |
| | Biotin-GNGKLIKGRTPIKFGKADCDRPPKHSQNGM-NH2 | (SEQ ID NO:64) | 3.0 |
| | Biotin-KLIKGRTPIKFGKADCDRPPKHSQNGMGK-NH2 | (SEQ ID NO:65) | 0.3 |
| | Biotin-KLIKGRTPIKFGKADCDRPPKHSQNGK-NH2 | (SEQ ID NO:66) | 0.3 |
| | Biotin-KGRTPIKFGKADCDRPPKHSQNGMGK-NH2 | (SEQ ID NO:67) | 3.0 |

TABLE 10-continued

Mapping of restrictocin L3 loop

| Peptide | Sequence | | Concentration (μM) |
|---|---|---|---|
| | Biotin-KLIKGRTPIKFGKADCDRPPKHSGK-NH2 | (SEQ ID NO:68) | 0.3 |
| | Biotin-KLIKGRTPIKFGKARCRRPPKHSGK-NH2 | (SEQ ID NO:69) | 0.3 |
| | Biotin-KLIKGRTPIKFGK-NH2 | (SEQ ID NO:70) | |

TABLE 11

Translocation activity of transport peptides
Other heparin binding peptides

| Name | Code | Sequence | | Concentration (μM) |
|---|---|---|---|---|
| HRSV-G, type A | MDN-12 | Biotin-KRIPNKKPGKKTTTKPTKKPTIKTTKKDLKPQTTKPK-NH2 | (SEQ ID NO:36) | 1.0 |
| | MDN-13 | Biotin-KRIPNKKPGKKTTTKPTKKPTIKTTKKDLK-NH2 | (SEQ ID NO:71) | 1.0 |
| | MDP-04 | Biotin-KRIPNKKPGKKTTTKPTKKPTIKTTKK-NH2 | (SEQ ID NO:72) | 0.3 |
| | MDP-08 | Biotin-KRIPNKKPGKKTTTKPTKKPTIK-NH2 | (SEQ ID NO:73) | 0.3 |
| | MDP-19 | Biotin-KRIPNKKPGKKTTTKPTKK-NH2 | (SEQ ID NO:74) | 0.3 |
| | MDP-32 | Biotin-KRIPNKKPGKKT-NH2 | (SEQ ID NO:42) | 0.03 |
| | MDS-34 | Biotin-KRIPNKKPGKK-NH2 | (SEQ ID NO:9) | 0.03 |
| | MDS-36 | Biotin-KRIPNKKPKK | (SEQ ID NO:38) | 0.03 |
| | MDS-09 | Biotin-KKPGKKTTTKPTKKPTIKTTKK-NH2 | (SEQ ID NO:75) | 0.3 |
| | MDS-23 | Biotin-KKPGKKTTTKPTKK-NH2 | (SEQ ID NO:76) | 0.3 |
| | | Biotin-KKTTTKPTKK-NH2 | (SEQ ID NO:77) | |
| | MDS-37 | Biotin-KKPTIKTTKK-NH2 | (SEQ ID NO:78) | 0.3 |
| HRSV-G, type B, region 1 | MDP-21 | Biotin-KSICKTIPSNKPKKK-NH2 | (SEQ ID NO:37) | 1.0 |
| | MDS-35 | Biotin-KTIPSNKPKKK-NH2 | (SEQ ID NO:10) | 0.1 |
| HRSV-G, type B, region 2 | | Biotin-KPRSKNPPKKPK | (SEQ ID NO:11) | |

NLS and DNA/RNA-Binding Peptides

| Name | Sequence | | Concentration (μM) |
|---|---|---|---|
| HIV-1 Rev | Biotin-DTRQARRNRRRRWRERQRAAAAR-NH2 | (SEQ ID NO:79) | 0.1 |
| | Biotin-RQARRNRRRRWR-NH2 | (SEQ ID NO:30) | 0.3/0.1 |
| RSG-1,2 | Biotin-DRRRRGSRPSGAERRRRRAAAA-NH2 | (SEQ ID NO:80) | 0.1 |
| | Biotin-RRRRGSRPSGAERRRRR-NH2 | (SEQ ID NO:81) | 1.0/0.3 |
| HIV-1 tat/tar | Biotin-RPRGTRGKGRRIRR-NH2 | (SEQ ID NO:82) | 0.3 |
| Bacteriophage lambda N peptide | Biotin-QTRRRERRAEKQAQW-NH2 | (SEQ ID NO:34) | 1.0 |
| | Biotin-RRRERRAEK-NH2 | (SEQ ID NO:83) | 1.0 |

| Name | Sequence | | Concentration (μM) |
|---|---|---|---|
| Flockhouse virus peptide | Biotin-NRTRRNRRRVR-NH2 | (SEQ ID NO:33) | 0.03 |
| Monopartite, NLS simian virus 40 large T antigen | Biotin-PKKKRKV-NH2 | (SEQ ID NO:28) | 0.1 |
| Bipartite | Biotin-KRPAAIKKAGQAKKKK-NH2 | (SEQ ID NO:29) | 0.1 |
| Herpesvirus 8 k8 protein (res. 124–135) | Biotin-TRRSKRRSHRKF-NH2 | (SEQ ID NO:32) | 0.1 |

Proteolytic cleavage site of viral surgace protein

| Alpha virus E3 | Biotin-KCPSRRPKR-NH2 | (SEQ ID NO:35) | 3.0 |
|---|---|---|---|

Antibacterial peptide

| Antibacterial peptide Buforin | Biotin-RAGLQFPVGRVHRLLRK-NH2 | (SEQ ID NO:84) | 3.0 |
|---|---|---|---|

TABLE 12

Peptide concentration that inhibits cell growth

| Cell type | $E^{ms}$ peptide (191–227) (μM) | $E^{ms}$ peptide (194–220) (μM) |
|---|---|---|
| HeLa | 50 | 40 |
| EBTr | 50 | 60 |

TABLE 13

Antibacterial, effect of $E^{ms}$ or L3 peptides

| Peptide[1] | MIC (ug/ml)[2] |
|---|---|
| 191–227 | 47 |
| 191–227 | 91 |
| 194–230 | 93 |
| 184–223 | 46 |
| 181–220 | 51 |
| 177–216 | 224 |
| 172–211 | >500 |
| 191–223 | 41 |

TABLE 13-continued

Antibacterial, effect of $E^{ms}$ or L3 peptides

| Peptide[1] | MIC (ug/ml)[2] |
|---|---|
| 191–220 | 47 |
| 191–216 | 95 |
| 191–211 | 395 |
| 194–220 | 50 |
| 194–218 | 25 |
| 196–220 | 25 |
| 199–220 | 23 |
| 202–220 | 179 |
| 205–220 | >500 |
| L3 | >500 |

[1]Same peptides as in Table 8.
[2]Minimal inhibitory concentration needed to inhibit bacterial growth.

What is claimed is:

1. An isolated peptide consisting of an amino acid sequence that is at least 70% identical to an amino acid sequence selected from the group of amino acid sequences consisting of from about amino acid position 194 to about amino acid position 220 in a pestiviral $E^{ms}$ protein RNase;

from about amino acid position 59 to about amino acid position 88 in an L3 loop of a cytotoxic RNase of a ribosome-inactivating protein; and mixtures thereof.

2. The isolated peptide of claim 1 consisting of an amino acid sequence that is at least 85% identical to said selected amino acid sequence.

3. The isolated peptide of claim 1 consisting of an amino acid sequence selected from the group of amino acid sequences consisting of
from about amino acid position 194 to about amino acid position 220 in a pestiviral $E^{ms}$ protein RNase;
from about amino acid position 59 to about amino acid position 88 in an L3 loop of a cytotoxic RNase of a ribosome-inactivating protein; and mixtures thereof.

4. The isolated peptide of claim 1, wherein said amino acid sequence is selected from the group consisting of SEQ ID NO:1; SEQ ID NO:2; SEQ ID NO:3; SEQ ID NO:4; SEQ ID NO:5; SEQ ID NO:6; SEQ ID NO:7; and SEQ ID NO:8.

5. An isolated peptide consisting of a reversed amino acid sequence to one of the group of amino acid sequences consisting of from about amino acid position 194 to about amino acid position 220 in a pestiviral $E^{ms}$ protein RNase;

from about amino acid position 59 to about amino acid position 88 in an L3 loop of a cytotoxic RNase of a ribosome-inactivating protein;

wherein, further, D-amino acids are used instead of L-amino acids.

6. The isolated peptide of claim 5, wherein said amino acid sequence is selected from the group consisting of: SEQ ID NO: 1; SEQ ID NO:2; SEQ ID NO:3; SEQ ID NO:4; SEQ ID NO:5; SEQ ID NO:6; SEQ ID NO:7; and SEQ ID NO:8.

7. In combination, the isolated peptide of claim 1, together with a compound for delivery.

8. The combination of claim 7 further comprising means for targeting said combination to a specific site.

9. A pharmaceutical composition comprising:

a peptide with a length of up to 51 amino acid residues having heparin-binding activity, said peptide comprising an amino acid sequence selected from the group of amino acid sequences consisting of from about amino acid position 194 to about amino acid position 220 in a pestiviral $E^{ms}$ protein RNase;

from about amino acid position 59 to about amino acid position 88 in an L3 loop of a cytotoxic RNase of a ribosome-inactivating protein; and a compound for delivery.

10. The pharmaceutical composition of claim 9, wherein the peptide comprises an amino acid sequence selected from the group consisting of: SEQ ID NO:1; SEQ ID NO:2; SEQ ID NO:3; SEQ ID NO:4; SEQ ID NO:5; SEQ ID NO:6; SEQ ID NO:7; and SEQ ID NO: 8.

11. A method of eliciting antibiotic activity in a subject, said method comprising:

administering to the subject a peptide consisting of an amino acid sequence selected from the group of amino acid sequences consisting of from about amino acid position 194 to about amino acid position 220 in a pestiviral $E^{ms}$ protein RNase;

from about amino acid position 59 to about amino acid position 88 in an L3 loop of a cytotoxic RNase of a ribosome-inactivating protein; and mixtures of any thereof.

12. The method according to claim 11, wherein the amino acid sequence is selected from the group consisting of: SEQ ID NO:1; SEQ ID NO:2; SEQ ID NO:3; SEQ ID NO:4; SEQ ID NO:5; SEQ ID NO:6; SEQ ID NO:7; and SEQ ID NO:8.

13. A method for translocating a compound through a cell's membrane, said method comprising:

providing said compound with an isolated peptide consisting of an amino acid sequence selected from the group of amino acid sequences consisting of from about amino acid position 194 to about amino acid position 220 in a pestiviral $E^{ms}$ protein RNase;

from about amino acid position 59 to about amino acid position 88 in an L3 loop of a cytotoxic RNase of a ribosome-inactivating protein; and contacting said compound and said isolated peptide with the cell.

14. The method according to claim 13, wherein the isolated peptide comprises an amino acid sequence selected from the group consisting of: SEQ ID NO:1; SEQ ID NO:2; SEQ ID NO:3; SEQ ID NO:4; SEQ ID NO:5; SEQ ID NO:6; SEQ ID NO:7; and SEQ ID NO:8.

15. The method according to claim 13, wherein said compound has a molecular weight of less than about 600 kD.

16. An isolated peptide consisting of an amino acid sequence located at about amino acid position 194 to about amino acid position 220 in a pestiviral $E^{ms}$ protein RNase, wherein the isolated peptide has anti-bacterial activity for a gram-negative bacterium as determined by an anti-microbial assay comprising mixing the isolated peptide with a gram-negative bacterial suspension in a culture, incubating the culture overnight, and determining an absorbance of the culture.

17. The isolated peptide of claim 16, wherein the amino acid sequence is selected from the group consisting of SEQ ID NOS:1, 2, 3, and 4.

18. The isolated peptide of claim 16, wherein the amino acid sequence is SEQ ID NO:1.

19. An isolated peptide having anti-bacterial activity for a gram-negative bacterium as determined by an anti-microbial assay comprising mixing the isolated peptide with a gram-negative bacterial suspension in a culture, incubating the culture overnight, and determining an absorbance of the culture, the isolated peptide consisting of an amino acid sequence selected from the group of amino acid sequences consisting of from about amino acid position 194 to about amino acid position 220 in a pestiviral E$^{ms}$ protein RNase;

from about amino acid position 59 to about amino acid position 88 in an L3 loop of a cytotoxic RNase of a ribosome-inactivating protein; and mixtures of any thereof.

20. An isolated peptide consisting of a reversed amino acid sequence to one of the group of amino acid sequences consisting of from about amino acid position 194 to about amino acid position 220 in a pestiviral E$^{ms}$ protein RNase; and from about amino acid position 59 to about amino acid position 88 in an L3 loop of a cytotoxic RNase of a ribosome-inactivating protein;

wherein, D-amino acids are used instead of L-amino acids.

21. A composition comprising:

a compound for delivery into a cell; and an isolated peptide of claim 2.

22. The composition of claim 21, wherein said isolated peptide has an amino acid sequence selected from the group consisting of SEQ ID NOS:1, 2, 3, and 4.

23. The composition of claim 22, wherein the amino acid sequence is SEQ ID NO:1.

* * * * *

SEQUENCE LISTING

<160> NUMBER OF SEQ ID NOS: 86

<210> SEQ ID NO 1
<211> LENGTH: 27
<212> TYPE: PRT
<213> ORGANISM: Artificial Sequence
<220> FEATURE:
<223> OTHER INFORMATION: Description of Artificial Sequence: transport peptide module of CSFV Erns protein

<400> SEQUENCE: 1

Arg Gln Gly Ala Ala Arg Val Thr Ser Trp Leu Gly Arg Gln Leu Arg
1               5                   10                  15

```
Ile Ala Gly Lys Arg Leu Glu Gly Arg Ser Lys
            20                  25

<210> SEQ ID NO 2
<211> LENGTH: 27
<212> TYPE: PRT
<213> ORGANISM: Artificial Sequence
<220> FEATURE:
<223> OTHER INFORMATION: Description of Artificial Sequence: transport
      peptide module of BDVD-1 Erns protein

<400> SEQUENCE: 2

Arg Gln Gly Thr Ala Lys Leu Thr Thr Trp Leu Gly Lys Gln Leu Gly
 1               5                  10                  15

Ile Leu Gly Lys Lys Leu Glu Asn Lys Ser Lys
            20                  25

<210> SEQ ID NO 3
<211> LENGTH: 27
<212> TYPE: PRT
<213> ORGANISM: Artificial Sequence
<220> FEATURE:
<223> OTHER INFORMATION: Description of Artificial Sequence: transport
      peptide module of BVDV-2 Erns protein

<400> SEQUENCE: 3

Arg Val Gly Thr Ala Lys Leu Thr Thr Trp Leu Gly Lys Gln Leu Gly
 1               5                  10                  15

Ile Leu Gly Lys Lys Leu Glu Asn Lys Thr Lys
            20                  25

<210> SEQ ID NO 4
<211> LENGTH: 27
<212> TYPE: PRT
<213> ORGANISM: Artificial Sequence
<220> FEATURE:
<223> OTHER INFORMATION: Description of Artificial Sequence: transport
      peptide module of BDV Erns protein

<400> SEQUENCE: 4

Arg Gln Gly Ala Ala Lys Leu Thr Ser Trp Leu Gly Lys Gln Leu Gly
 1               5                  10                  15

Ile Met Gly Lys Lys Leu Glu His Lys Ser Lys
            20                  25

<210> SEQ ID NO 5
<211> LENGTH: 32
<212> TYPE: PRT
<213> ORGANISM: Artificial Sequence
<220> FEATURE:
<223> OTHER INFORMATION: Description of Artificial Sequence: peptide
      from Rnase L3 loop from Restrictocin, Mitogillin, and Toxin Aspf1

<400> SEQUENCE: 5

Gly Asn Gly Lys Leu Ile Lys Gly Arg Thr Pro Ile Lys Phe Gly Lys
 1               5                  10                  15

Ala Asp Cys Asp Arg Pro Pro Lys His Ser Gln Asn Gly Met Gly Lys
            20                  25                  30

<210> SEQ ID NO 6
<211> LENGTH: 32
<212> TYPE: PRT
<213> ORGANISM: Artificial Sequence
<220> FEATURE:
<223> OTHER INFORMATION: Description of Artificial Sequence: peptide
``` from Rnase L3 loop from Alpha-sarcin

<400> SEQUENCE: 6

Gly Asp Gly Lys Leu Ile Pro Gly Arg Thr Pro Ile Lys Phe Gly Lys
1               5                   10                  15

Ser Asp Cys Asp Arg Pro Pro Lys His Ser Lys Asp Gly Asn Gly Lys
            20                  25                  30

<210> SEQ ID NO 7
<211> LENGTH: 32
<212> TYPE: PRT
<213> ORGANISM: Artificial Sequence
<220> FEATURE:
<223> OTHER INFORMATION: Description of Artificial Sequence: peptide
      from Rnase L3 loop from Gigantin

<400> SEQUENCE: 7

Gly Glu Gly Lys Ile Leu Lys Gly Arg Thr Pro Ile Lys Phe Gly Lys
1               5                   10                  15

Ser Asp Cys Asp Arg Pro Pro Lys His Ser Lys Asp Gly Asn Gly Lys
            20                  25                  30

<210> SEQ ID NO 8
<211> LENGTH: 32
<212> TYPE: PRT
<213> ORGANISM: Artificial Sequence
<220> FEATURE:
<223> OTHER INFORMATION: Description of Artificial Sequence: peptide
      from Rnase L3 loop from Clavin

<400> SEQUENCE: 8

Gly Asp Gly Lys Ile Leu Lys Gly Arg Thr Pro Ile Lys Trp Gly Asn
1               5                   10                  15

Ser Asp Cys Asp Arg Pro Pro Lys His Ser Lys Asn Gly Asp Gly Lys
            20                  25                  30

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence:
      heparin-binding peptide from HRSV-G, type A

<400> SEQUENCE: 9

Lys Arg Ile Pro Asn Lys Lys Pro Gly Lys Lys
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence:
      heparin-binding peptide from HRSV-G, type B, region 1

<400> SEQUENCE: 10

Lys Thr Ile Pro Ser Asn Lys Pro Lys Lys Lys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence:

heparin-binding peptide from HRSV-G, type B, region 2

<400> SEQUENCE: 11

Lys Pro Arg Ser Lys Asn Pro Pro Lys Lys Pro Lys
 1               5                  10

<210> SEQ ID NO 12
<211> LENGTH: 32
<212> TYPE: PRT
<213> ORGANISM: Artificial Sequence
<220> FEATURE:
<223> OTHER INFORMATION: Description of Artificial Sequence: transport
      peptide module of CSFV Erns protein

<400> SEQUENCE: 12

Glu Asn Ala Arg Gln Gly Ala Ala Arg Val Thr Ser Trp Leu Gly Arg
 1               5                  10                  15

Gln Leu Arg Ile Ala Gly Lys Arg Leu Glu Gly Arg Ser Lys Thr Trp
            20                  25                  30

<210> SEQ ID NO 13
<211> LENGTH: 32
<212> TYPE: PRT
<213> ORGANISM: Artificial Sequence
<220> FEATURE:
<223> OTHER INFORMATION: Description of Artificial Sequence: transport
      peptide module of BVDV-1 Erns protein

<400> SEQUENCE: 13

Glu Gly Ala Arg Gln Gly Thr Ala Lys Leu Thr Thr Trp Leu Gly Lys
 1               5                  10                  15

Gln Leu Gly Ile Leu Gly Lys Lys Leu Glu Asn Lys Ser Lys Thr Trp
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: Description of Artificial Sequence: transport
      peptide module of BVDV-2 Erns protein

<400> SEQUENCE: 14

Glu Gly Ala Arg Val Gly Thr Ala Lys Leu Thr Thr Trp Leu Gly Lys
 1               5                  10                  15

Gln Leu Gly Ile Leu Gly Lys Lys Leu Glu Asn Lys Thr Lys Ala Trp
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: Description of Artificial Sequence: transport
      peptide module of BDV Erns protein

<400> SEQUENCE: 15

Glu Asn Ala Arg Gln Gly Ala Ala Lys Leu Thr Ser Trp Leu Gly Lys
 1               5                  10                  15

Gln Leu Gly Ile Met Gly Lys Lys Leu Glu His Lys Ser Lys Thr Trp
            20                  25                  30

<210> SEQ ID NO 16
<211> LENGTH: 37
<212> TYPE: PRT

```
<213> ORGANISM: Artificial Sequence
<220> FEATURE:
<223> OTHER INFORMATION: Description of Artificial Sequence: transport
      peptide module of CSFV Erns protein

<400> SEQUENCE: 16
```

Glu Asn Ala Arg Gln Gly Ala Ala Arg Val Thr Ser Trp Leu Gly Arg
1               5                   10                  15

Gln Leu Arg Ile Ala Gly Lys Arg Leu Glu Gly Arg Ser Lys Thr Trp
            20                  25                  30

Phe Gly Ala Tyr Ala
        35

```
<210> SEQ ID NO 17
<211> LENGTH: 37
<212> TYPE: PRT
<213> ORGANISM: Artificial Sequence
<220> FEATURE:
<223> OTHER INFORMATION: Description of Artificial Sequence: transport
      peptide module of BVDV-1 Erns protein

<400> SEQUENCE: 17
```

Glu Gly Ala Arg Gln Gly Thr Ala Lys Leu Thr Thr Trp Leu Gly Lys
1               5                   10                  15

Gln Leu Gly Ile Leu Gly Lys Lys Leu Glu Asn Lys Ser Lys Thr Trp
            20                  25                  30

Phe Gly Ala Tyr Ala
        35

```
<210> SEQ ID NO 18
<211> LENGTH: 37
<212> TYPE: PRT
<213> ORGANISM: Artificial Sequence
<220> FEATURE:
<223> OTHER INFORMATION: Description of Artificial Sequence: transport
      peptide module of BVDV-2 Erns protein

<400> SEQUENCE: 18
```

Glu Gly Ala Arg Val Gly Thr Ala Lys Leu Thr Thr Trp Leu Gly Lys
1               5                   10                  15

Gln Leu Gly Ile Leu Gly Lys Lys Leu Glu Asn Lys Thr Lys Ala Trp
            20                  25                  30

Phe Gly Ala His Ala
        35

```
<210> SEQ ID NO 19
<211> LENGTH: 37
<212> TYPE: PRT
<213> ORGANISM: Artificial Sequence
<220> FEATURE:
<223> OTHER INFORMATION: Description of Artificial Sequence: transport
      peptide module of BDV Erns protein

<400> SEQUENCE: 19
```

Glu Asn Ala Arg Gln Gly Ala Ala Lys Leu Thr Ser Trp Leu Gly Lys
1               5                   10                  15

Gln Leu Gly Ile Met Gly Lys Lys Leu Glu His Lys Ser Lys Thr Trp
            20                  25                  30

Phe Gly Ala Asn Ala
        35

```
<210> SEQ ID NO 20
<211> LENGTH: 51
```

<212> TYPE: PRT
<213> ORGANISM: Artificial Sequence
<220> FEATURE:
<223> OTHER INFORMATION: Description of Artificial Sequence: transport peptide module of CSFV Erns protein

<400> SEQUENCE: 20

Asp Thr Ala Leu Tyr Leu Val Asp Gly Met Thr Asn Thr Ile Glu Asn
 1               5                  10                  15

Ala Arg Gln Gly Ala Ala Arg Val Thr Ser Trp Leu Gly Arg Gln Leu
            20                  25                  30

Arg Ile Ala Gly Lys Arg Leu Glu Gly Arg Ser Lys Thr Trp Phe Gly
        35                  40                  45

Ala Tyr Ala
    50

<210> SEQ ID NO 21
<211> LENGTH: 51
<212> TYPE: PRT
<213> ORGANISM: Artificial Sequence
<220> FEATURE:
<223> OTHER INFORMATION: Description of Artificial Sequence: transport peptide module of BVDV-1 Erns protein

<400> SEQUENCE: 21

Asp Thr Thr Leu Tyr Leu Val Asp Gly Leu Thr Asn Ser Leu Glu Gly
 1               5                  10                  15

Ala Arg Gln Gly Thr Ala Lys Leu Thr Thr Trp Leu Gly Lys Gln Leu
            20                  25                  30

Gly Ile Leu Gly Lys Lys Leu Glu Asn Lys Ser Lys Thr Trp Phe Gly
        35                  40                  45

Ala Tyr Ala
    50

<210> SEQ ID NO 22
<211> LENGTH: 51
<212> TYPE: PRT
<213> ORGANISM: Artificial Sequence
<220> FEATURE:
<223> OTHER INFORMATION: Description of Artificial Sequence: transport peptide module of BVDV-2 Erns protein

<400> SEQUENCE: 22

Glu Thr Ala Ile Gln Leu Leu Asp Gly Ala Thr Asn Thr Ile Glu Gly
 1               5                  10                  15

Ala Arg Val Gly Thr Ala Lys Leu Thr Thr Trp Leu Gly Lys Gln Leu
            20                  25                  30

Gly Ile Leu Gly Lys Lys Leu Glu Asn Lys Thr Lys Ala Trp Phe Gly
        35                  40                  45

Ala His Ala
    50

<210> SEQ ID NO 23
<211> LENGTH: 51
<212> TYPE: PRT
<213> ORGANISM: Artificial Sequence
<220> FEATURE:
<223> OTHER INFORMATION: Description of Artificial Sequence: transport peptide module of BDV Erns protein

<400> SEQUENCE: 23

Asp Thr Ala Leu Tyr Val Val Asp Gly Val Thr Asn Thr Val Glu Asn
 1               5                  10                  15

Ala Arg Gln Gly Ala Ala Lys Leu Thr Ser Trp Leu Gly Lys Gln Leu
            20                  25                  30

Gly Ile Met Gly Lys Lys Leu Glu His Lys Ser Lys Thr Trp Phe Gly
        35                  40                  45

Ala Asn Ala
    50

<210> SEQ ID NO 24
<211> LENGTH: 23
<212> TYPE: PRT
<213> ORGANISM: Artificial Sequence
<220> FEATURE:
<223> OTHER INFORMATION: Description of Artificial Sequence: Magainin
      Erns transport peptide module

<400> SEQUENCE: 24

Gly Ile Gly Lys Phe Leu His Ser Ala Gly Lys Phe Gly Lys Ala Phe
1               5                   10                  15

Val Gly Glu Ile Met Lys Ser
            20

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: transport
      peptide module of CSFV Erns protein

<400> SEQUENCE: 25

Gly Arg Gln Leu Arg Ile Ala Gly Lys Arg Leu Glu Gly Arg Ser Lys
1               5                   10                  15

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence:
      5' and 3' FITC labeled oligonucleotide

<400> SEQUENCE: 26
gtccaccgag gctagctaca acgacccta tat                                    33

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: movin
      peptide with mutations

<400> SEQUENCE: 27

Arg Ser Arg Gly Arg Leu Arg Arg Gly Ala Ile Arg Leu Gln Arg Gly
1               5                   10                  15

Lys

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: NLS peptide
      of simian virus 40 large T antigen

```
<400> SEQUENCE: 28

Pro Lys Lys Lys Arg Lys Val
1               5

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: NLS peptide
      of HIV-1 Rev

<400> SEQUENCE: 29

Lys Arg Pro Ala Ala Ile Lys Lys Ala Gly Gln Ala Lys Lys Lys Lys
1               5                   10                  15

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: NLS peptide
      of HIV-1 Rev

<400> SEQUENCE: 30

Arg Gln Ala Arg Arg Asn Arg Arg Arg Arg Trp Arg
1               5                   10

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: synthetic
      peptide RSG-1.2

<400> SEQUENCE: 31

Asp Arg Arg Arg Arg Gly Ser Arg Pro Ser Gly Ala Glu Arg Arg Arg
1               5                   10                  15

Arg Arg

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: NLS peptide
      of human herpesvirus-8 K8 protein

<400> SEQUENCE: 32

Thr Arg Arg Ser Lys Arg Arg Ser His Arg Lys Phe
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: RNA binding
      peptide domain of flockhouse virus

<400> SEQUENCE: 33

Asn Arg Thr Arg Arg Asn Arg Arg Arg Val Arg
1               5                   10

<210> SEQ ID NO 34
```

```
<211> LENGTH: 15
<212> TYPE: PRT
<213> ORGANISM: Artificial Sequence
<220> FEATURE:
<223> OTHER INFORMATION: Description of Artificial Sequence: RNA binding
      peptide domain of bacteriophage lambda-N

<400> SEQUENCE: 34

Gln Thr Arg Arg Arg Glu Arg Arg Ala Glu Lys Gln Ala Gln Trp
 1               5                  10                  15

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: peptide of
      western equine encephalitis virus E3 surface protein

<400> SEQUENCE: 35

Lys Cys Pro Ser Arg Arg Pro Lys Arg
 1               5

<210> SEQ ID NO 36
<211> LENGTH: 37
<212> TYPE: PRT
<213> ORGANISM: Artificial Sequence
<220> FEATURE:
<223> OTHER INFORMATION: Description of Artificial Sequence:
      heparin-binding domain peptide of HRSV-G, type A

<400> SEQUENCE: 36

Lys Arg Ile Pro Asn Lys Lys Pro Gly Lys Lys Thr Thr Thr Lys Pro
 1               5                  10                  15

Thr Lys Lys Pro Thr Ile Lys Thr Thr Lys Lys Asp Leu Lys Pro Gln
                20                  25                  30

Thr Thr Lys Pro Lys
            35

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence:
      heparin-binding domain peptide of HRSV-G, type B

<400> SEQUENCE: 37

Lys Ser Ile Cys Lys Thr Ile Pro Ser Asn Lys Pro Lys Lys Lys
 1               5                  10                  15

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence:
      heparin-binding domain peptide of HRSV-G, type A

<400> SEQUENCE: 38

Lys Arg Ile Pro Asn Lys Lys Pro Lys Lys
 1               5                  10

<210> SEQ ID NO 39
<211> LENGTH: 16
<212> TYPE: PRT
<213> ORGANISM: Artificial Sequence
```

```
<220> FEATURE:
<223> OTHER INFORMATION: Description of Artificial Sequence: movin
      transport peptide module

<400> SEQUENCE: 39

Gly Arg Gln Leu Arg Ile Ala Gly Arg Arg Leu Arg Gly Arg Ser Arg
 1               5                  10                  15

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: single
      point substitution mutation peptide of movin

<400> SEQUENCE: 40

Gly Arg Gln Leu Arg Arg Ala Gly Arg Arg Leu Arg Arg Arg Ser Arg
 1               5                  10                  15

<210> SEQ ID NO 41
<211> LENGTH: 36
<212> TYPE: PRT
<213> ORGANISM: Artificial Sequence
<220> FEATURE:
<223> OTHER INFORMATION: Description of Artificial Sequence:
      heparin-binding domain peptide of HRSV-G, type A

<400> SEQUENCE: 41

Lys Arg Ile Pro Asn Lys Lys Pro Gly Lys Lys Thr Thr Thr Pro Thr
 1               5                  10                  15

Lys Lys Pro Thr Ile Lys Thr Thr Lys Lys Asp Leu Lys Pro Gln Thr
                20                  25                  30

Thr Lys Pro Lys
            35

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence:
      heparin-binding domain peptide of HRSV-G, type A

<400> SEQUENCE: 42

Lys Arg Ile Pro Asn Lys Lys Pro Gly Lys Lys Thr
 1               5                  10

<210> SEQ ID NO 43
<211> LENGTH: 37
<212> TYPE: PRT
<213> ORGANISM: Artificial Sequence
<220> FEATURE:
<223> OTHER INFORMATION: Description of Artificial Sequence: transport
      peptide module of CSFV Erns protein
<220> FEATURE:
<221> NAME/KEY: MISC_FEATURE
<222> LOCATION: (26)
<223> OTHER INFORMATION: Xaa is a mixture of Gly or Arg

<400> SEQUENCE: 43

Glu Asn Ala Arg Gln Gly Ala Ala Arg Val Thr Ser Trp Leu Gly Arg
 1               5                  10                  15

Gln Leu Ser Thr Ala Gly Lys Arg Leu Glu Xaa Arg Ser Lys Thr Trp
                20                  25                  30

Phe Gly Ala Tyr Ala
            35
```

<210> SEQ ID NO 44
<211> LENGTH: 37
<212> TYPE: PRT
<213> ORGANISM: Artificial Sequence
<220> FEATURE:
<223> OTHER INFORMATION: Description of Artificial Sequence: transport
      peptide module of BDV Erns protein

<400> SEQUENCE: 44

Glu Asn Ala Arg Gln Gly Ala Ala Lys Leu Thr Ser Trp Leu Gly Lys
 1               5                  10                  15

Gln Leu Gly Ile Met Gly Lys Lys Leu Glu His His Ser Lys Thr Trp
            20                  25                  30

Phe Gly Ala Asn Ala
        35

<210> SEQ ID NO 45
<211> LENGTH: 37
<212> TYPE: PRT
<213> ORGANISM: Artificial Sequence
<220> FEATURE:
<223> OTHER INFORMATION: Description of Artificial Sequence: transport
      peptide module of BVDV strain M96751 Erns protein

<400> SEQUENCE: 45

Glu Gly Ala Arg Gln Gly Thr Ala Lys Leu Thr Thr Trp Leu Gly Lys
 1               5                  10                  15

Gln Leu Gly Thr Ala Gly Lys Lys Leu Glu Asn Lys Ser Lys Thr Trp
            20                  25                  30

Phe Gly Ala Tyr Ala
        35

<210> SEQ ID NO 46
<211> LENGTH: 40
<212> TYPE: PRT
<213> ORGANISM: Artificial Sequence
<220> FEATURE:
<223> OTHER INFORMATION: Description of Artificial Sequence: transport
      peptide module of CSFV Erns protein

<400> SEQUENCE: 46

Asp Gly Met Thr Asn Thr Ile Glu Asn Ala Arg Gln Gly Ala Ala Arg
 1               5                  10                  15

Val Thr Ser Trp Leu Gly Arg Gln Leu Arg Ile Ala Gly Lys Arg Leu
            20                  25                  30

Glu Gly Arg Ser Lys Thr Trp Phe
        35                  40

<210> SEQ ID NO 47
<211> LENGTH: 40
<212> TYPE: PRT
<213> ORGANISM: Artificial Sequence
<220> FEATURE:
<223> OTHER INFORMATION: Description of Artificial Sequence: transport
      peptide module of CSFV Erns protein

<400> SEQUENCE: 47

Tyr Leu Leu Asp Gly Met Thr Asn Thr Ile Glu Asn Ala Arg Gln Gly
 1               5                  10                  15

Ala Ala Arg Val Thr Ser Trp Leu Gly Arg Gln Leu Arg Ile Ala Gly
            20                  25                  30

Lys Arg Leu Glu Gly Arg Ser Lys
        35                  40

<210> SEQ ID NO 48
<211> LENGTH: 40
<212> TYPE: PRT
<213> ORGANISM: Artificial Sequence
<220> FEATURE:
<223> OTHER INFORMATION: Description of Artificial Sequence: transport
      peptide module of CSFV Erns protein

<400> SEQUENCE: 48

Asp Thr Ala Leu Tyr Leu Leu Asp Gly Met Thr Asn Thr Ile Glu Asn
 1               5                  10                  15

Ala Arg Gln Gly Ala Ala Arg Val Thr Ser Trp Leu Gly Arg Gln Leu
            20                  25                  30

Arg Ile Ala Gly Lys Arg Leu Glu
        35                  40

<210> SEQ ID NO 49
<211> LENGTH: 40
<212> TYPE: PRT
<213> ORGANISM: Artificial Sequence
<220> FEATURE:
<223> OTHER INFORMATION: Description of Artificial Sequence: transport
      peptide module of CSFV Erns protein

<400> SEQUENCE: 49

Gly Ser Leu Leu Gln Asp Thr Ala Leu Tyr Leu Leu Asp Gly Met Thr
 1               5                  10                  15

Asn Thr Ile Glu Asn Ala Arg Gln Gly Ala Ala Arg Val Thr Ser Trp
            20                  25                  30

Leu Gly Arg Gln Leu Arg Ile Ala
        35                  40

<210> SEQ ID NO 50
<211> LENGTH: 33
<212> TYPE: PRT
<213> ORGANISM: Artificial Sequence
<220> FEATURE:
<223> OTHER INFORMATION: Description of Artificial Sequence: transport
      peptide module of CSFV Erns protein

<400> SEQUENCE: 50

Glu Asn Ala Arg Gln Gly Ala Ala Arg Val Thr Ser Trp Leu Gly Arg
 1               5                  10                  15

Gln Leu Arg Ile Ala Gly Lys Arg Leu Glu Gly Arg Ser Lys Thr Trp
            20                  25                  30

Phe

<210> SEQ ID NO 51
<211> LENGTH: 30
<212> TYPE: PRT
<213> ORGANISM: Artificial Sequence
<220> FEATURE:
<223> OTHER INFORMATION: Description of Artificial Sequence: transport
      peptide module of CSFV Erns protein

<400> SEQUENCE: 51

Glu Asn Ala Arg Gln Gly Ala Ala Arg Val Thr Ser Trp Leu Gly Arg
 1               5                  10                  15

Gln Leu Arg Ile Ala Gly Lys Arg Leu Glu Gly Arg Ser Lys
            20                  25                  30

<210> SEQ ID NO 52
<211> LENGTH: 26
<212> TYPE: PRT
<213> ORGANISM: Artificial Sequence
<220> FEATURE:
<223> OTHER INFORMATION: Description of Artificial Sequence: transport peptide module of CSFV Erns protein

<400> SEQUENCE: 52

Glu Asn Ala Arg Gln Gly Ala Ala Arg Val Thr Ser Trp Leu Gly Arg
 1               5                  10                  15

Gln Leu Arg Ile Ala Gly Lys Arg Leu Glu
            20                  25

<210> SEQ ID NO 53
<211> LENGTH: 21
<212> TYPE: PRT
<213> ORGANISM: Artificial Sequence
<220> FEATURE:
<223> OTHER INFORMATION: Description of Artificial Sequence: transport peptide module of CSFV Erns protein

<400> SEQUENCE: 53

Glu Asn Ala Arg Gln Gly Ala Ala Arg Val Thr Ser Trp Leu Gly Arg
 1               5                  10                  15

Gln Leu Arg Ile Ala
            20

<210> SEQ ID NO 54
<211> LENGTH: 25
<212> TYPE: PRT
<213> ORGANISM: Artificial Sequence
<220> FEATURE:
<223> OTHER INFORMATION: Description of Artificial Sequence: transport peptide module of CSFV Erns protein

<400> SEQUENCE: 54

Gly Ala Ala Arg Val Thr Ser Trp Leu Gly Arg Gln Leu Arg Ile Ala
 1               5                  10                  15

Gly Lys Arg Leu Glu Gly Arg Ser Lys
            20                  25

<210> SEQ ID NO 55
<211> LENGTH: 22
<212> TYPE: PRT
<213> ORGANISM: Artificial Sequence
<220> FEATURE:
<223> OTHER INFORMATION: Description of Artificial Sequence: transport peptide module of CSFV Erns protein

<400> SEQUENCE: 55

Arg Val Thr Ser Trp Leu Gly Arg Gln Leu Arg Ile Ala Gly Lys Arg
 1               5                  10                  15

Leu Glu Gly Arg Ser Lys
            20

<210> SEQ ID NO 56
<211> LENGTH: 19
<212> TYPE: PRT
<213> ORGANISM: Artificial Sequence
<220> FEATURE:
<223> OTHER INFORMATION: Description of Artificial Sequence: transport peptide module of CSFV Erns protein

<400> SEQUENCE: 56

-continued

Ser Trp Leu Gly Arg Gln Leu Arg Ile Ala Gly Lys Arg Leu Glu Gly
1               5                   10                  15

Arg Ser Lys

<210> SEQ ID NO 57
<211> LENGTH: 23
<212> TYPE: PRT
<213> ORGANISM: Artificial Sequence
<220> FEATURE:
<223> OTHER INFORMATION: Description of Artificial Sequence: transport
      peptide module of CSFV Erns protein

<400> SEQUENCE: 57

Arg Arg Val Thr Ser Trp Leu Gly Arg Gln Leu Arg Ile Ala Gly Lys
1               5                   10                  15

Arg Leu Glu Gly Arg Ser Lys
            20

<210> SEQ ID NO 58
<211> LENGTH: 22
<212> TYPE: PRT
<213> ORGANISM: Artificial Sequence
<220> FEATURE:
<223> OTHER INFORMATION: Description of Artificial Sequence: transport
      peptide module of CSFV Erns protein

<400> SEQUENCE: 58

Arg Val Arg Ser Trp Leu Gly Arg Gln Leu Arg Ile Ala Gly Lys Arg
1               5                   10                  15

Leu Glu Gly Arg Ser Lys
            20

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: transport
      peptide module of CSFV Erns protein

<400> SEQUENCE: 59

Gly Arg Gln Leu Arg Ile Ala Gly Lys Arg Leu Arg Gly Arg Ser Lys
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: movin
      peptide

<400> SEQUENCE: 60

Gly Arg Gln Leu Arg Arg Ala Gly Arg Arg Leu Arg Gly Arg Ser Arg
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: movin
      peptide

<400> SEQUENCE: 61

Gly Arg Gln Leu Arg Ile Ala Gly Arg Arg Leu Arg Arg Arg Ser Arg

-continued

```
    1               5                   10                  15
```

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: movin
      peptide

<400> SEQUENCE: 62

```
Arg Gln Leu Arg Ile Ala Gly Arg Arg Leu Arg Gly Arg Ser Arg
 1               5                   10                  15
```

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: movin
      peptide

<400> SEQUENCE: 63

```
Arg Ser Arg Gly Arg Leu Arg Arg Gly Ala Ile Arg Leu Gln Arg Gly
 1               5                   10                  15
```

<210> SEQ ID NO 64
<211> LENGTH: 30
<212> TYPE: PRT
<213> ORGANISM: Artificial Sequence
<220> FEATURE:
<223> OTHER INFORMATION: Description of Artificial Sequence: peptide
      from Rnase L3 loop from Restrictocin

<400> SEQUENCE: 64

```
Gly Asn Gly Lys Leu Ile Lys Gly Arg Thr Pro Ile Lys Phe Gly Lys
 1               5                   10                  15

Ala Asp Cys Asp Arg Pro Pro Lys His Ser Gln Asn Gly Met
            20                  25                  30
```

<210> SEQ ID NO 65
<211> LENGTH: 29
<212> TYPE: PRT
<213> ORGANISM: Artificial Sequence
<220> FEATURE:
<223> OTHER INFORMATION: Description of Artificial Sequence: peptide
      from Rnase L3 loop from Restrictocin

<400> SEQUENCE: 65

```
Lys Leu Ile Lys Gly Arg Thr Pro Ile Lys Phe Gly Lys Ala Asp Cys
 1               5                   10                  15

Asp Arg Pro Pro Lys His Ser Gln Asn Gly Met Gly Lys
            20                  25
```

<210> SEQ ID NO 66
<211> LENGTH: 27
<212> TYPE: PRT
<213> ORGANISM: Artificial Sequence
<220> FEATURE:
<223> OTHER INFORMATION: Description of Artificial Sequence: peptide
      from Rnase L3 loop from Restrictocin

<400> SEQUENCE: 66

```
Lys Leu Ile Lys Gly Arg Thr Pro Ile Lys Phe Gly Lys Ala Asp Cys
 1               5                   10                  15

Asp Arg Pro Pro Lys His Ser Gln Asn Gly Lys
            20                  25
```

```
            20                  25

<210> SEQ ID NO 67
<211> LENGTH: 26
<212> TYPE: PRT
<213> ORGANISM: Artificial Sequence
<220> FEATURE:
<223> OTHER INFORMATION: Description of Artificial Sequence: peptide
      from Rnase L3 loop from Restrictocin

<400> SEQUENCE: 67

Lys Gly Arg Thr Pro Ile Lys Phe Gly Lys Ala Asp Cys Asp Arg Pro
  1               5                  10                  15

Pro Lys His Ser Gln Asn Gly Met Gly Lys
            20                  25

<210> SEQ ID NO 68
<211> LENGTH: 25
<212> TYPE: PRT
<213> ORGANISM: Artificial Sequence
<220> FEATURE:
<223> OTHER INFORMATION: Description of Artificial Sequence: peptide
      from Rnase L3 loop from Restrictocin

<400> SEQUENCE: 68

Lys Leu Ile Lys Gly Arg Thr Pro Ile Lys Phe Gly Lys Ala Asp Cys
  1               5                  10                  15

Asp Arg Pro Pro Lys His Ser Gly Lys
            20                  25

<210> SEQ ID NO 69
<211> LENGTH: 25
<212> TYPE: PRT
<213> ORGANISM: Artificial Sequence
<220> FEATURE:
<223> OTHER INFORMATION: Description of Artificial Sequence: peptide
      from Rnase L3 loop from Restrictocin

<400> SEQUENCE: 69

Lys Leu Ile Lys Gly Arg Thr Pro Ile Lys Phe Gly Lys Ala Arg Cys
  1               5                  10                  15

Arg Arg Pro Pro Lys His Ser Gly Lys
            20                  25

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence: peptide
      from Rnase L3 loop from Restrictocin

<400> SEQUENCE: 70

Lys Leu Ile Lys Gly Arg Thr Pro Ile Lys Phe Gly Lys
  1               5                  10

<210> SEQ ID NO 71
<211> LENGTH: 30
<212> TYPE: PRT
<213> ORGANISM: Artificial Sequence
<220> FEATURE:
<223> OTHER INFORMATION: Description of Artificial Sequence:
      heparin-binding domain peptide of HRSV-G, type A

<400> SEQUENCE: 71

Lys Arg Ile Pro Asn Lys Lys Pro Gly Lys Lys Thr Thr Thr Lys Pro
```

```
                   1               5              10              15

Thr Lys Lys Pro Thr Ile Lys Thr Thr Lys Asp Leu Lys
                  20              25              30

<210> SEQ ID NO 72
<211> LENGTH: 27
<212> TYPE: PRT
<213> ORGANISM: Artificial Sequence
<220> FEATURE:
<223> OTHER INFORMATION: Description of Artificial Sequence:
      heparin-binding domain peptide of HRSV-G, type A

<400> SEQUENCE: 72

Lys Arg Ile Pro Asn Lys Lys Pro Gly Lys Lys Thr Thr Thr Lys Pro
 1               5              10                          15

Thr Lys Lys Pro Thr Ile Lys Thr Thr Lys Lys
                 20              25

<210> SEQ ID NO 73
<211> LENGTH: 23
<212> TYPE: PRT
<213> ORGANISM: Artificial Sequence
<220> FEATURE:
<223> OTHER INFORMATION: Description of Artificial Sequence:
      heparin-binding domain peptide of HRSV-G, type A

<400> SEQUENCE: 73

Lys Arg Ile Pro Asn Lys Lys Pro Gly Lys Lys Thr Thr Thr Lys Pro
 1               5              10                          15

Thr Lys Lys Pro Thr Ile Lys
                 20

<210> SEQ ID NO 74
<211> LENGTH: 19
<212> TYPE: PRT
<213> ORGANISM: Artificial Sequence
<220> FEATURE:
<223> OTHER INFORMATION: Description of Artificial Sequence:
      heparin-binding domain peptide of HRSV-G, type A

<400> SEQUENCE: 74

Lys Arg Ile Pro Asn Lys Lys Pro Gly Lys Lys Thr Thr Thr Lys Pro
 1               5              10                          15

Thr Lys Lys

<210> SEQ ID NO 75
<211> LENGTH: 22
<212> TYPE: PRT
<213> ORGANISM: Artificial Sequence
<220> FEATURE:
<223> OTHER INFORMATION: Description of Artificial Sequence:
      heparin-binding domain peptide of HRSV-G, type A

<400> SEQUENCE: 75

Lys Lys Pro Gly Lys Lys Thr Thr Thr Lys Pro Thr Lys Lys Pro Thr
 1               5              10                          15

Ile Lys Thr Thr Lys Lys
                 20

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence:
``` heparin-binding domain peptide of HRSV-G, type A

<400> SEQUENCE: 76

Lys Lys Pro Gly Lys Lys Thr Thr Thr Lys Pro Thr Lys Lys
 1               5                  10

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence:
      heparin-binding domain peptide of HRSV-G, type A

<400> SEQUENCE: 77

Lys Lys Thr Thr Thr Lys Pro Thr Lys Lys
 1               5                  10

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence:
      heparin-binding domain peptide of HRSV-G, type A

<400> SEQUENCE: 78

Lys Lys Pro Thr Ile Lys Thr Thr Lys Lys
 1               5                  10

<210> SEQ ID NO 79
<211> LENGTH: 23
<212> TYPE: PRT
<213> ORGANISM: Artificial Sequence
<220> FEATURE:
<223> OTHER INFORMATION: Description of Artificial Sequence: NLS peptide
      of HIV-1 Rev

<400> SEQUENCE: 79

Asp Thr Arg Gln Ala Arg Arg Asn Arg Arg Arg Trp Arg Glu Arg
 1               5                  10                  15

Gln Arg Ala Ala Ala Ala Arg
            20

<210> SEQ ID NO 80
<211> LENGTH: 22
<212> TYPE: PRT
<213> ORGANISM: Artificial Sequence
<220> FEATURE:
<223> OTHER INFORMATION: Description of Artificial Sequence: synthetic
      peptide RSG-1.2

<400> SEQUENCE: 80

Asp Arg Arg Arg Arg Gly Ser Arg Pro Ser Gly Ala Glu Arg Arg
 1               5                  10                  15

Arg Arg Ala Ala Ala Ala
            20

<210> SEQ ID NO 81
<211> LENGTH: 17
<212> TYPE: PRT
<213> ORGANISM: Artificial Sequence
<220> FEATURE:
<223> OTHER INFORMATION: Description of Artificial Sequence: synthetic
      peptide RSG-1.2

<400> SEQUENCE: 81

Arg Arg Arg Arg Gly Ser Arg Pro Ser Gly Ala Glu Arg Arg Arg
1               5                   10                  15

Arg

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: peptide
      from HIV-1 tat/tar

<400> SEQUENCE: 82

Arg Pro Arg Gly Thr Arg Gly Lys Gly Arg Arg Ile Arg Arg
1               5                   10

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: RNA
      binding peptide domain of bacteriophage lambda-N

<400> SEQUENCE: 83

Arg Arg Arg Glu Arg Arg Ala Glu Lys
1               5

<210> SEQ ID NO 84
<211> LENGTH: 17
<212> TYPE: PRT
<213> ORGANISM: Artificial Sequence
<220> FEATURE:
<223> OTHER INFORMATION: Description of Artificial Sequence: Buforin
      antibacterial peptide

<400> SEQUENCE: 84

Arg Ala Gly Leu Gln Phe Pro Val Gly Arg Val His Arg Leu Leu Arg
1               5                   10                  15

Lys

<210> SEQ ID NO 85
<211> LENGTH: 37
<212> TYPE: PRT
<213> ORGANISM: Artificial Sequence
<220> FEATURE:
<223> OTHER INFORMATION: Description of Artificial Sequence:
      artificially synthesized, isolated or recombinant peptide

<400> SEQUENCE: 85

Glu Ser Ala Arg Gln Gly Thr Ala Lys Leu Thr Thr Trp Leu Gly Arg
1               5                   10                  15

Gln Leu Lys Lys Leu Gly Lys Lys Leu Glu Asn Lys Ser Lys Thr Trp
            20                  25                  30

Phe Gly Ala Tyr Ala
        35

<210> SEQ ID NO 86
<211> LENGTH: 32
<212> TYPE: PRT
<213> ORGANISM: Artificial Sequence
<220> FEATURE:
<223> OTHER INFORMATION: Description of Artificial Sequence:
      artificially synthesized, isolated or recombinant peptide -continued

```
<400> SEQUENCE: 86

Asp Gly Asn Gly Lys Leu Ile Lys Gly Arg Thr Pro Ile Lys Phe Gly
1               5                   10                  15

Lys Ala Asp Cys Asp Arg Pro Pro Lys His Ser Gln Asn Gly Met Lys
            20                  25                  30
```